United States Patent
Gao et al.

(10) Patent No.: US 7,208,611 B2
(45) Date of Patent: Apr. 24, 2007

(54) PLATINUM-CONTAINING COMPOUNDS EXHIBITING CYTOSTATIC ACTIVITY, SYNTHESIS AND METHODS OF USE

(75) Inventors: Qingzhi Gao, Cupertino, CA (US); Mark A. Gallop, Los Altos, CA (US); Jia-Ning Xiang, Palo Alto, CA (US)

(73) Assignee: XenoPort, Inc., Santa Clara, CA (US)

(*) Notice: Subject to any disclaimer, the term of this patent is extended or adjusted under 35 U.S.C. 154(b) by 0 days.

(21) Appl. No.: 11/361,435

(22) Filed: Feb. 23, 2006

(65) Prior Publication Data
US 2006/0205677 A1    Sep. 14, 2006

Related U.S. Application Data

(60) Provisional application No. 60/655,766, filed on Feb. 23, 2005.

(51) Int. Cl.
*C07F 15/00* (2006.01)
*A61K 31/28* (2006.01)

(52) U.S. Cl. .......... 549/211; 556/137; 514/492

(58) Field of Classification Search ............ 556/137; 549/211; 514/492
See application file for complete search history.

(56) References Cited

U.S. PATENT DOCUMENTS

| | | | |
|---|---|---|---|
| 3,811,444 A | 5/1974 | Heller et al. | |
| 3,962,414 A | 6/1976 | Michaels | |
| 3,992,518 A | 11/1976 | Chien et al. | |
| 4,066,747 A | 1/1978 | Capozza | |
| 4,070,347 A | 1/1978 | Schmitt | |
| 4,079,038 A | 3/1978 | Choi et al. | |
| 4,083,949 A | 4/1978 | Benedikt | |
| 4,093,709 A | 6/1978 | Choi et al. | |
| 4,284,579 A * | 8/1981 | Meischen et al. | 556/19 |
| 4,895,935 A | 1/1990 | Talebian et al. | |
| 4,895,936 A | 1/1990 | Talebian et al. | |
| 4,937,358 A * | 6/1990 | Bitha et al. | 549/206 |
| 4,946,954 A | 8/1990 | Talebian et al. | |
| 4,956,459 A | 9/1990 | Talebian et al. | |
| 4,968,826 A * | 11/1990 | Totani et al. | 556/137 |
| 5,091,521 A | 2/1992 | Kolar et al. | |
| 5,698,155 A | 12/1997 | Grosswald et al. | |
| 7,001,888 B2 * | 2/2006 | Tidmarsh et al. | 514/23 |
| 2003/0152518 A1 | 8/2003 | Tidmarsh et al. | |

(Continued)

FOREIGN PATENT DOCUMENTS

WO    WO 1994/12285    6/1994

(Continued)

OTHER PUBLICATIONS

Alderman, "A Review of cellulose Ethers in Hydrophilic Matrices dor Oral controlled-Release Dosage Forms," *Int. J. Pharm. Tech. & Prod. Mfr.* 1984, 5(3) 1-9.

(Continued)

*Primary Examiner*—Porfirio Nazario-Gonzalez
(74) *Attorney, Agent, or Firm*—Dorsey & Whitney LLP

(57) ABSTRACT

Platinum containing compounds exhibiting cytostatic activity, methods of synthesizing platinum-containing compounds exhibiting cytostatic activity pharmaceutical compositions comprising platinum containing compounds, and methods of using such compounds and compositions for treating cancer are disclosed.

24 Claims, 4 Drawing Sheets

U.S. PATENT DOCUMENTS

| | | |
|---|---|---|
| 2004/0029815 A1 | 2/2004 | Tidmarsh et al. |
| 2006/0089341 A1* | 4/2006 | Kratz et al. .................. 514/184 |

FOREIGN PATENT DOCUMENTS

| | | |
|---|---|---|
| WO | WO 2000/48572 | 8/2000 |
| WO | WO 2000/54588 | 9/2000 |
| WO | WO 2003/059149 | 7/2003 |
| WO | WO 2003/082301 | 10/2003 |
| WO | WO 2004/062604 | 7/2004 |
| WO | WO 2004/064734 | 8/2004 |
| WO | WO 2004/064735 | 8/2004 |
| WO | WO 2004/064736 | 8/2004 |
| WO | WO 2004/081181 | 9/2004 |
| WO | WO 2004/087075 | 10/2004 |
| WO | WO 2005/011931 | 2/2005 |
| WO | WO 2005/119261 | 12/2005 |
| WO | WO 2005/120498 | 12/2005 |

OTHER PUBLICATIONS

Altomare et al., "Highly Water-Soluble Derivatives of Anaesthetic Agent Propofol: in vitro and invitro evaluation of cyclic amino esters," *European Journal of Pharmaceutical Sciences*, 2003, 20, 1, 17-26.

Anderson et al., "α-Amino Acid Phenolic Ester Derivatives: Novel Water-Soluble General Anesthetic Agents Which Allosterically Modulate $GABA_A$ Receptors," *J. Med. Chem.* 2001, 44, 3582-3591.

Arp, "Tumor Models: Assessing toxicity in Efficacy Studies," *Toxicol Pathol.*, 1999, 27(1), 121-122.

Balimane et al., "Involvement of multiple transporters in the oral absorption of nucleoside analogues," *Adv Drug Deliv Rev.* Oct. 18, 1999;39(1-3):183-209.

Bamba et al., "Release Mechanisms in Gelforming Sustained Release Preparations," *Int. J. Pharm.* 1979, 2, 307.

Banaszcryk et al., "Propofol Phosphate, a Water-Soluble Propofol Prodrug: In Vivo Evaluation," *Anesth. Analg.* 2002, 95, 1285-1292.

Becker et al., "Human Thioredoxin Reductase Is Efficiently Inhabited by (2,2':6'2"-Trepyridine) Platinum (II) Complexes. Possible Implications for Novel Antitumor Strategy," *J. Med. Chem.*, 2001, 44, 2784-2792.

Beilstein, Beilstein Handbook of Organic Chemistry, Beilsein Institute of Organic Chemistry, Frankfurt, Germany. vol. 27, Part 26, 1979.

Borgeat et al., "Preliminary Communication: Adjuvant Propofol Enables Better Control of Nausea and Emesid Secondary to Chemotherapy for Breast Cancer," *Can. J. Anaesth.* 1994, 1117-1119.

Borgeat et al., "Propofol improves patient comfort during cisplatin chemotherapy. A pilot study," *Oncology* 1993, 50, 456-459.

Brandel et al., "14-3-3 Protein Cerebrospinal Fluid Detection in Human Growth Hormone- Treated Creutzfeldt-Jakob Disease Patients," Ann. Neurol. 2001, 49, 257-260.

Briggs et al., "An adverse reaction to the administration of disoprofol (Diprivan)," *Anaesthesia* 1982, 37, 1099-1101.

Brooker et al., "Propofol Maintenance to Reduce Postoperatiove Emesis in Thyroidectomy Patients: A Group Sequential Comparison with Isoflurane/Nitrous Oxide," *Anaesth. Intensive Care* 1998, 26, 625-629.

Brown et al., "Role of Propofol in Refractory Status Epilepticus," *Pharmacother.* 1998, 32, 1053-1059.

Canetta et al., Carboplatin: Current Satatus and Future Prospects,*Cancer Treat Rev.*, 1988, 15, Sup. B, 17-32.

Coleman et al., "Polymer Review: A Practical Guide to Polymer Miscibility," *Polymers*, 1990, 31, 1187-1231.

De Jonghe et al., "Further Evidence that Neurofilament Light Chain Gene Mutations Can Cause Charcot-Marie Tooth Disease Type 2E," Ann. Neurol., 2001, 49-245-249.

De la Cruz et al., "The Effect of Propofol on Oxidative Stress in Platelets from Surgical Patients," *Anesth. Analg.* 1999, 89, 1050-1055.

During et al., "Controlled release of dopamine from a polymeric brain implant: in vivo characterization," 1989, *Ann. Neurol.* 25:351.

Feiser et al., "Reagents for Organic Synthesis," vols. 1-17, Wiley Interscience, vol. 2, 2004.

Felmeister, "Powders," Remington's Pharmaceutical Sciences, 1970, 14th Edition, 1626-1627, Mac Publishing Company, Easton, Pennsylvania.

Fincher, "Particle Size of Drugs and Its Relationship to Absorption and Activity," *J. Pharm. Sci.* 1968, 57, 1825-1835.

Gan et al., "Determination of Plasma Concentrations of Propofol Associated with 50% Reduction in Postoperative Nausea," *Anesthesiology*, 1997, 87, 779-784.

Gennaro, "Remington's Pharmaceutical Sciences," Philadelphia College of Pharmacy and Science, 19th Edition, 1995.

Gonzalez et al., "Resolution of Acid Strength in Non-Aqueous Acid-Base Titrations," *Analytica Chimica Acta*, 1991, 281, 179-183.

Goodson, in "Medical Applications of Controlled Release," *supra*, vol. 2, pp. 115-138 (1984).

Greene et al. *Protective groups in Organic Chemistry*, Wiley, 2nd ed., 1991.

Grothey, "Oxaliplatin-Safety Profile: Neurotoxicity," *Semin. Oncol.* 2003, 30, 4 Sup. 15, 5-13.

Hand et al., "Compound Heterozygous D90A and D96N SODI Mutations in a Recessive Amyotrophic Lateral Sclerosis Family," Ann. Neurol, 2001, 49, 267-271.

Harrison et al., *Compendium of Synthetic Organic Methods*, vols. 1-8, John Wiley and Sons, 1971-1996.

Hasan et al., "Comparison of the Effects of the Propofol and Thiopental on the Pattern of Maximal Electroshock Seizures in a Rat," *Pharmacol. Toxicol.* 1994, 74, 50-53.

Hashimoto et al., "Abnormal Activity in the Globus Pallidus in Off-Period Dystonia," *Ann. Neurol.*, 2001, 49, 242-245.

Hegedus et al., *Compendium of Organic Synthetic Methods*, Wiley-Interscience Publication, vol. 3, 1977.

Hoes et al., *The Application of Drug-Polymer Conjugates in Chemotherapy*, Drug Carrier Systems, 1989, 9, 57-100.

Holtkamp et al., "Propofol in subanesthetic doses terminates status epilepticus in a rodent model," *Ann. Neurol.* 2001, 49, 260-263.

Howard et al., "Intercerebral Drug Delivery in Rats with Lesion-Induced Memory Deficits," 1989, *J. Neurosurg.* 71:105-112.

Krusz et al., "Intravenous Propofol: Unique Effectiveness in Treating Intractable Migraine," *Headache* 2000, 40, 224-230.

Kuisma et al., "Propofol in Prewhospital Treatment of Convulsive Status Epilepticus," *Epilepsia* 1995, 36, 1241-1243.

Langer et al. "Medical Applications of Controlled Release," , CRC Press, Boca Raton, Florida (1974).

Langer et al., "Chemical and Physical Structure of Polymers as Carriers for Controlled Relaease of Bioactive Agents: A Review," *J Macromol. Sci. Rev. Macromol Chem.* 1983, 23:61.

Langer, "New Method of Drug Delivery," 1990, *Science* 249:1527-1533.

Langley et al., "Propofol. A review of its pharmacodynamic and pharmacokinetic properties and use as an intravenous anaesthetic," *Drugs* 1988, 35, 334-372.

Larock, "Comprehensive Organic Transformations: A Guide to Functional Group Preparations," (VCH Publishers, 1989).

Lee et al., "Inhibitors of Acyl-Coa: Cholesterosl O-Acyl Transferase (ACAT) as Hypocholeserolemic Agents. CI-1011: An Acyl Sulfamate with Unique Cholsterol-Lowering Activity in Animals Fed Noncholesterol-Supplemented Diets," *Journal of Medicinal Chemistry, An American Chemical Society*, vol. 39, No. 26, 1996, 5031-5034.

Leong et al., "Polymeric Controlled Drug Delivery," *Adv. Drug Delivery Rev.* 1987, 1, 199-233.

Levy et al., "Inhibition of Calcification of Bioprosthetic Heart Valves by Local Controlled-Release Diphosphonate," *Science* 1985 228: 190-192.

Lu, "Dimensionless Presentation for Drug Release From a Coated Pure Drug Bead: 2 Experiment," *Int. J. Pharm.*, 1994, 112, 117-124.

March, *Advance Organic Chemistry*, Wiley Interscience, 1991.

Medina et al. "Glucose Transporters: Expression, Regulation and Cancer," *Biol. Res.*, 2002, 35, 9-26.

Minassian et al., "Laforinn Is a Cell Membrane and Endoplasmic Reticulum- Associated protein Tyrosine Phosphatase," *Ann. Neurol.* 2001, 49, 271-275.

Murphy et al., "The Antioxidant Potential of Propofol (2,6-Diisopropylphenol)," *Br. J. Anaesth.* 1992, 68, 613-618;.

Paquette, *Encyclopedia of Reagents for Organic Synthesis,* John Wiley & Sons, 1995.

Pastor et al., "Familial Atypical Progressive Supranuclear Palsy Associated with Homozigosity for the delN296 Mutation in the Tau Gene," Ann. Neurol., 2001, 49, 263-267.

Pharmaceutical Sciences by Remington, 14th ed, pp. 1626-1628 (1970).

Pharmaceutical Sciences by Remington, 17th Ed, Ch. 90, 1603-1625 (1985).

Picard et al., "Prevention of Pain on Injection with Propofol: A Quantitative Systematic Review," 2000, 90, 963-969.

Pop et al., "Synthesis and Preliminary Pharmacological Evaluation of Some Chemical Delivery Systems of 2,6-Diisopropylphenol (Propofol)," *Med. Chem. Res.* 1992, 2, 16-21.

Prestayko et al., "Cisplatin (*cis*-diamminedchloroplatinum II)," *Cancer Treat. Rev.* 1979, 6, 17-39.

Raleigh et al., "Searching for the Link Between Hypoxia and Poor Prognoses in Human Tumors," *Proc. Amer. Assoc. Cancer Research Annual Meeting,* 1999, 40, 39.

Raoof et al., "In Vivo Assessment of Intestinal Hepatic, and Pulmonary First Pass Metabolism of Propofol in the Rat," *Pharm. Res.* 1996, 13, 891-895.

Roff et al., Handbook of Common Polymers: Pibres, Films, Plastics and Rubbers, CRC Press, 1971.

Rosenberg, "Fundamental Studies With Cisplatin," *Cancer* 1985, 55, 2303-2316.

Rosoff, *Controlled Release of Drugs: Polymers and Aggregate Systems,* Chap. 2, 53-95, 1989.

Sagara et al., "Propofol Hemisuccinate Protects Neuronal Cells from Oxidative Injury," *J. Neurochem.* 1999, 73, 2524-2530.

Saudek et al., "A Preliminary Trial of the Programmable Implantable Medication System for Insulin Delivery," *N. Engl. J. Med.,* 1989, 321: 574.

Sefton, "Implantable Pumps," *CRC Crit Ref Biomed. Eng.* 1987, 14:201.

Simonian et al., "Oxidative Stress in Neurodegenerative Disease," Pharmacol. Toxicol. 1996, 36, 83-106.

Sleijfer et al., "Cisplatin: a Review of Clinical Applications and Renal Toxicity," *Pharm Weekbl Sci.* 1985, 7, 237-244.

Smith, *Compendium of Organic Synthetic Methods,* Wiley & Sons, vol. 6, 1988.

Smith, *Compendium of Organic Synthetic Methods,* Wiley & Sons, vol. 7, 1992.

Smith, *Compendium of Organic Synthetic Methods,* Wiley & Sons, vol. 8, 1995.

Smolen et al, Drug Product Design and Performance, *Controlled Drug Bioavailability,* Smolen and Ball (eds.), Wiley, New York (1984).

Sutton et al., "Anti-Yo Antibodies and the Cerebelar Degeneration in a Man with Adenocarcinoma of the Esophagus," Ann. Neurol., 2001, 49, 253-257.

Talebian et al., "Murine Anti-Tumor Activity of New Water Soluble Platinum(II) Complexes with Reduced Toxicity," *Anticancer Drug Des.,* 1990, 5, 371-378.

Theilheimer, *Theilheimer's Synthetic Methods of Organic Chemistry,* Karger, London, vol. 45, 1991.

Theilheimer, *Theilheimer's Synthetic Methods of Organic Chemistry,* Karger, London, vol. 67, 2005.

Tomioka et al., "Propofol Is Effective in Chemotherapy-Induced Nausea and Vomiting: A Case Report with Quantitative Analysis," *Anesth. Analg.* 1999, 89, 798-799.

Tramer et al., "Propofol Anaesthesia and Postoperative Nausea and Vomiting Quantitative and Systemic Review of Randomized Controlled Studies," *Br. J. Anaesth.* 1997, 78, 247-255.

Trapani et al., "Propofol Analogues. Synthesis, Relationships Between Structure and Affinity for $GABA_A$ Receptors," *J. Med. Chem.* 1998, 41, 1846-1854.

Trapani et al., "Water—Soluble Salts of Aminoacid Esters of the Anaesthetic Agent Propofol," *Int. J. Pharm.* 1998, 175, 195-204.

Tromp et al., "The Beta-Glucuronyl-Based Prodrug Strategy Allows For Iis Application On Beta-Glucuronyl-Platinum Conjugates," *Bioorg. Med. Chem. Lett.,* 2004, 14, 4273-4276.

Trost et al, *Comprehensive Organic Synthesis,* Pergamon Press, vol. 9, 1991.

Uldry et al., "The SLC2 Family of Facilitated Hexose and Polyol Transporters," *Pflugers Arch.,* 2004, 447, 480-489.

Verma et al., "Osmotically Controlled Oral Drug Delivery," *Drug Dev. Ind. Pharm.,* 2000, 26:695-708.

Veronese et al., "Polyorganophosphazene Microspheres for Drug Release: Polymer Synthesis, Microsphere Preparation, In Vitro and In Vivo Naproxen Release," *Journal of Controlled Release,* 1998, 52,227-237.

Vetter et al., "Strategies of the Synthesis of Screening of Glycoconjugates. 1. A Library of Glycosylamines," *Bioconjug. Chem.* 1995, 6, 316-318.

Wade, *Compendium of Organic Synthetic Methods,* Wiley & Sons, vol. 4, 1980.

Wade, *Compendium of Organic Synthetic Methods,* Wiley & Sons, vol. 5, 1984.

Walder et al., "Seizure-like phenomena and propofol," *Neurology* 2002, 58, 1327-1332.

Walker et al., "Absence of Echovirus Sequences in Brain and the Spinal Cord of Amyotrophic Lateral Sclerosis Patients," Ann. Neurol., 2001, 49, 249-253.

Wang et al. "Propofol reduces infarct size and striatal dopamine accumulation following transient middle cerebral artery occlusion: a microdialysis study," *Eur. J. Pharmacol.* 2002, 452, 303-308.

Young et al., "Propofol neuroprotection in a rat model of ischaemia reperfusion injury," *Eur. J. Anaesthesiol.* 1997, 14, 320-326.

\* cited by examiner

PLATINUM-CONTAINING COMPOUNDS EXHIBITING CYTOSTATIC ACTIVITY, SYNTHESIS AND METHODS OF USE

This application claims benefit to U.S. Provisional Application No. 60/655,766 filed Feb. 23, 2005, which is incorporated by reference herein in its entirety.

Disclosed herein are platinum containing compounds exhibiting cytostatic activity, methods of synthesizing platinum-containing compounds exhibiting cytostatic activity, pharmaceutical composites comprising platinum-containing compounds, and methods of using such compounds and pharmaceutical compositions for treating cancer.

Since their introduction into clinical practice more than 20 years ago platinum drugs have dramatically enhanced the prognosis of patients with advanced germ cell tumors.

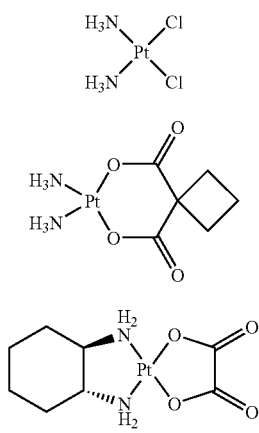

Cisplatin (1) has become a key ingredient in the chemotherapy of such cancers, whether gonadal or extragonadal in origin. The spectrum of antitumor efficacy of cisplatin includes testicular carcinoma, ovarian cancer, oropharyngeal carcinoma, bronchogenic carcinoma, cervical carcinoma, osteosacoma, melanoma, lymphoma, bladder carcinoma, and neuroblastoma (Rosenberg, *Cancer* 1985, 55, 2303–2316; Prestayko et al., *Cancer Treat. Rev.* 1979, 6, 17–39). However, the use of cisplatin can be associated with a serious adverse side effect profile, including emetogensis, nephrotoxicity, and neurological toxicity (Sleijfer et al., *Pharm Weekbl Sci.* 1985, 7, 237–244). The cytotoxicity of the platinum drugs has a complex etiology that is still only partially understood. Cytotoxicity of platinum drugs is known to be mediated in part via interactions with DNA nucleobases such as the formation of intrastrand crosslinks through displacement of anionic leaving groups from Pt by nucleophilic N-7 atoms of adjacent guanine bases. Carboplatin (2) is significantly less reactive towards hydrolysis and interaction with macromolecules (both DNA and proteins) than cisplatin and is also much less nephrotoxic and emetogenic than the latter drug (Canetta et al., *Cancer Treat Rev.* 1988, 15, Sup. B, 17–32). More recently, oxaliplatin (3) has become an integral part of various chemotherapy protocols, and in advanced colorectal cancer in particular. While oxaliplatin has only mild hematologic and gastrointestinal side effects, its dose-limiting toxicity is a cumulative sensory neurotoxicity that resembles that of cisplatin with the important difference of a more rapid and complete reversibility (Grothey, *Semin. Oncol.* 2003, 30, 4 Sup. 15, 5–13). The reversibility of neurotoxicity has been established in long-term follow-up of patients who have received adjuvant oxaliplatin-based chemotherapy. In addition, oxaliplatin can cause a unique, but frequent, acute sensory neuropathy that can be triggered or aggravated by exposure to cold, which is rapidly reversible, without persistent impairment of sensory function.

The undesired side effects of the existing platinum antitumor drugs, including cisplatin, carboplatin and oxaliplatin, often limit the usefulness of these powerful cytotoxic agents against solid tumors. It has recently been recognized that an effective mechanism for achieving more selective targeting of antitumor agents to cancer cells is to exploit the differential expression of nutrient transporter systems that frequently exists between cancerous and normal tissue (see PCT International Publication Nos. WO 2005-11931, WO 2005-120498, and WO 2005-119261, each of which is incorporated herein by reference in its entirety). The family of facilitated glucose transporters (GLUTs), which contains at least 14 members in humans (SLC2A1-14, GLUT1-14) include transporters that are highly expressed in cancer cells relative to normal cells in adjacent tissue (e.g. GLUT1, GLUT3 and GLUT5; see for example, Medina and Owen, *Biol. Res.* 2002, 35, 9–26). GLUT transporters have 12 putative transmembrane domains, with both the amino and carboxy termini located on the cytoplasmic side. Various GLUT transporters have been demonstrated to transport a variety of sugars such as glucose, 2-deoxyglucose, galactose, fructose, and inositol, and sugar analogs such as dehydroascorbate, glucosamine, and fluorodeoxyglucose. Transport is bidirectional, effecting transport either into or out of the cell depending on the substrate gradients (Uldry and Thorens, *Pflugers Arch.*, 2004, 447, 480–489). Conjugates of glucose and glucose derivatives and anti-cancer agents have been described (see U.S. Application Publication No. 2004-0029815).

The low solubility of the existing platinum antitumor drugs such as cisplatin, carboplatin and oxaliplatin is also disadvantageous. Previous attempts to increase the aqueous solubility of platinum anticancer drugs have included incorporation of carbohydrate moieties within the ligands bonded to the platinum center (see for example, Talebian et al., U.S. Pat. No. 4,895,935; Talebian et al., U.S. Pat. No. 4,895,936; Talebian et al., U.S. Pat. No. 4,946,954; Talebian et al., U.S. Pat. No. 4,956,459; Kolar et al., U.S. Pat. No. 5,091,521; Talebian et al., *Anticancer Drug Des.*, 1990, 5, 371–378; and Tromp et al., *Bioorg. Med. Chem. Lett.*, 2004, 14, 4273–4276).

Thus there is a need to identify new platinum complexes with antitumor activity that demonstrate good water solubility and possess therapeutic indices superior to existing clinically used agents.

Certain aspects of the present disclosure provide compounds of Formula (I):

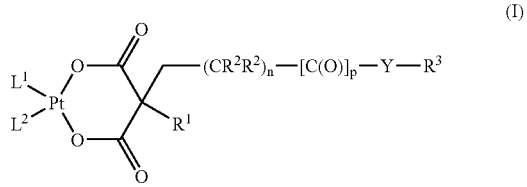

or a pharmaceutically acceptable salt thereof, or a pharmaceutically acceptable solvate of any of the foregoing, wherein:

n is an integer from 0 to 4;

p is chosen from 0 and 1;

$L^1$ and $L^2$ are each $NH_3$ or $L^1$ and $L^2$ together form a 1,2-cycloalkanediamine chosen from trans-(1R,2R)-cyclohexanediamine, trans-(1S,2S)-cyclohexanediamine, and cis-(R, S)-cyclohexanediamine;

$R^1$ is chosen from hydrogen and $C_{1-4}$ alkyl;

each $R^2$ is independently chosen from hydrogen and $C_{1-4}$ alkyl;

Y is chosen from —$NR^5$— and —O—;

$R^3$ is chosen from

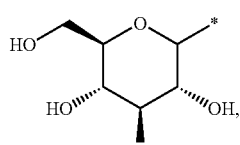
(II)

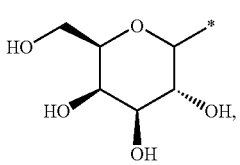
(III)

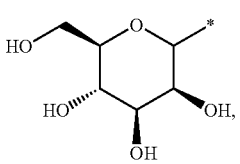
(IV)

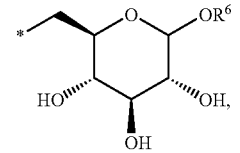
(V)

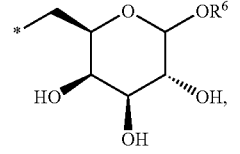
(VI)

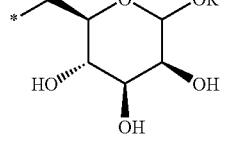
(VII)

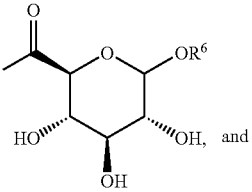
(VIII)

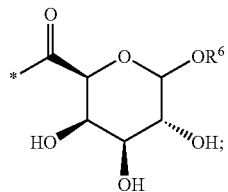
(IX)

wherein $R^6$ is chosen from hydrogen and $C_{1-4}$ alkyl; and $R^5$ is chosen from hydrogen and $C_{1-4}$ alkyl.

Certain aspects of the present disclosure provide compounds of Formula (X):

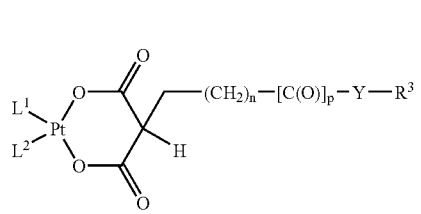
(X)

or a pharmaceutically acceptable salt thereof, or a pharmaceutically acceptable solvate of any of the foregoing, wherein:

n is chosen from 1 and 2;

p is chosen from 0 and 1;

$L^1$ and $L^2$ are each $NH_3$ or $L^1$ and $L^2$ together are trans-(1R,2R)-cyclohexanediamine;

Y is chosen from —NH— and —O—; and $R^3$ is chosen from

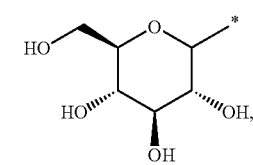
(II)

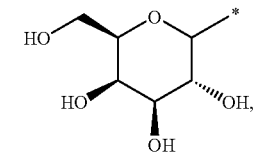
(III)

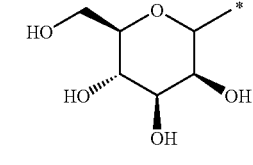
(IV)

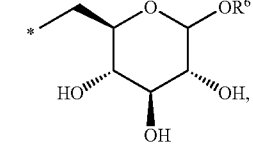
(V)

-continued

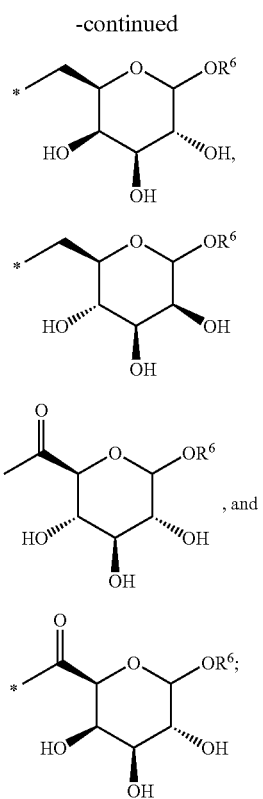

(VI)

(VII)

(VIII)

(IX)

wherein $R^6$ is chosen from hydrogen and methyl.

Certain aspects of the present disclosure provide compounds of Formula (XI):

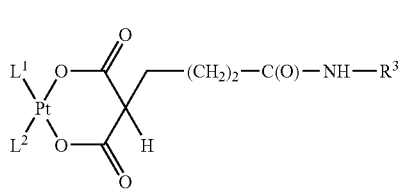

(XI)

or a pharmaceutically acceptable salt thereof, or a pharmaceutically acceptable solvate of any of the foregoing, wherein:

$L^1$ and $L^2$ are each $NH_3$ or $L^1$ and $L^2$ together form a 1,2-cycloalkanediamine chosen from trans-(1R,2R)-cyclohexanediamine, trans-(1S,2S)-cyclohexanediamine, and cis-(R,S)-cyclohexanediamine; and $R^3$ is

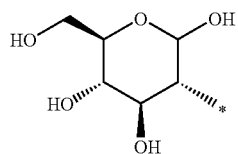

Certain aspects of the present disclosure provide pharmaceutical compositions comprising a compound of the present disclosure or a pharmaceutically acceptable salt thereof, or a pharmaceutically acceptable solvate of any of the foregoing, and a pharmaceutically acceptable vehicle such as a diluent, carrier, excipient or adjuvant.

Certain aspects of the present disclosure provide methods of treating cancer in a patient comprising administering to a patient in need of such treatment a therapeutically effective amount of a compound of the present disclosure.

Certain aspects of the present disclosure provide methods of treating cancer in a patient comprising administering to a patient in need of such treatment a therapeutically effective amount of a pharmaceutical composition of the present disclosure.

Additional embodiments of the invention are set forth in the description which follows, or may be learned by practice of the invention.

BRIEF DESCRIPTION OF THE DRAWINGS

The skilled artisan will understand that the drawings, described herein, are for illustration purposes only. The drawings are not intended to limit the scope of the present disclosure.

DETAILED DESCRIPTION

Definitions

Figure 1:
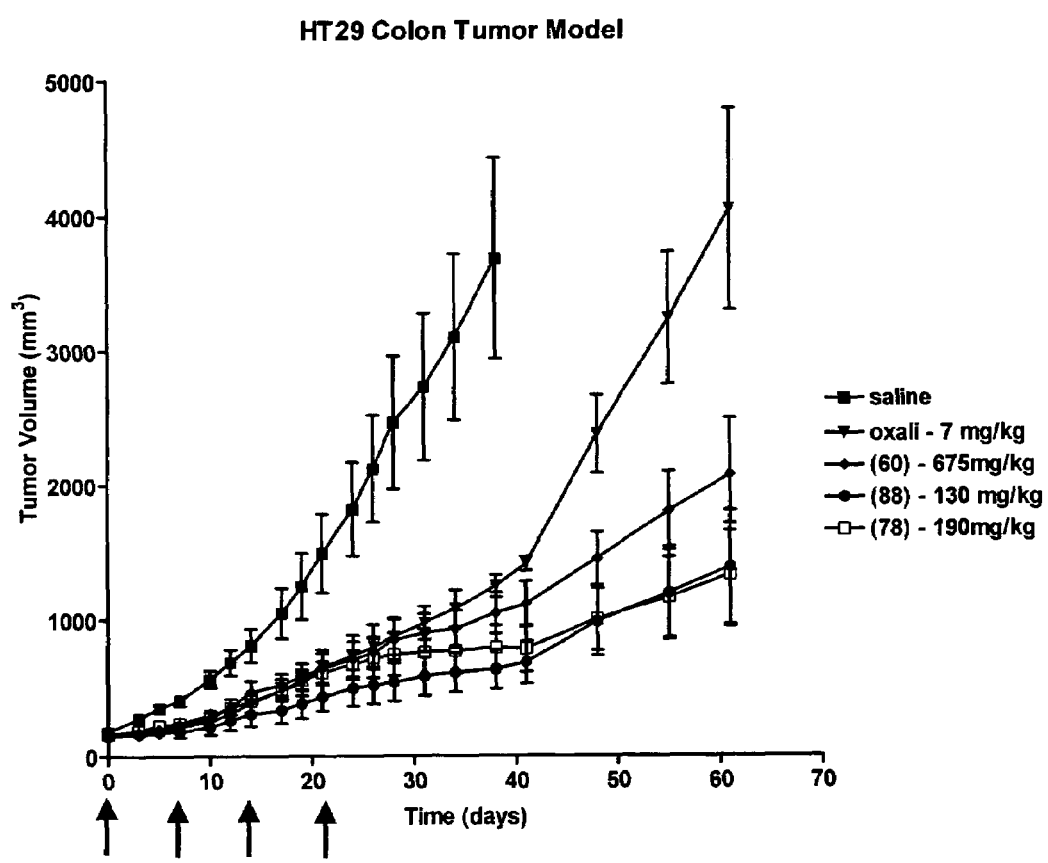
FIG. 1 shows percent tumor size in a HT29 colon tumor xenograph model during treatment with oxaliplatin or certain sugar platinum compounds of the present disclosure.

As used in the present specification, the following words and phrases are generally intended to have the meanings as set forth below, except to the extent that the context in which they are used indicates otherwise.

As used herein, when any variable occurs more than one time in a chemical formula, its definition on each occurrence is independent of its definition at every other occurrence. In accordance with the usual meaning of "a" and "the" in patents, reference to "a" compound or "the" compound is inclusive of one or more compounds. Unless otherwise specified the terms "compound" and "compounds" include all pharmaceutically acceptable forms of the disclosed structures salts, solvates, and the like.

"Alkyl" by itself or as part of another substituent refers to a saturated or unsaturated, branched, straight-chain or cyclic monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon—carbon bonds, groups having one or more double carbon—carbon bonds, groups having one or more triple carbon—carbon bonds and groups having mixtures of single, double and triple carbon—carbon bonds. Where a specific level of saturation is intended, the expressions "alkanyl," "alkenyl," and "alkynyl" are used. In certain embodiments, an alkyl group comprises from 1 to 20 carbon atoms, in certain embodiments, from 1 to 10 carbon atoms, and in certain embodiments, from 1 to 6 carbon atoms.

"Cancerous cell" refers to a cell that has lost or partially lost the ability to control cell division. A cancerous cell can be a cell line such as HeLa, MOLT4, and others, and can also be a cell obtained from a patient. A cancerous cell from a patient can be from a solid tumor (such as a tumor of the colon) or from a non-solid tissue such as blood (such as leukemia). A cancerous cell can be isolated from a human or animal, such as cells obtained from a tissue biopsy. A cancer cell can be present in a human or animal. Cancerous cells are also referred to as tumor cells.

Malignant cancers are those that invade surrounding tissues and metastasize (spread) to other body sites via the blood and lymphatic circulations. Metastasized cancers usually remain the same type of cell as the cells at the initial site of cancer development; for example, if breast cancer metastasizes to a lung, the cancer in the lung consists of breast cells. Benign cancers do not invade other tissues or spread, have a slower growth rate than malignant cancers, and in most cases are not fatal.

"Compounds" refers to compounds encompassed by structural Formulae (I)—(XI) disclosed herein and includes any specific compounds within these formulae for which the structure is disclosed herein. Compounds may be identified either by their chemical structure and/or chemical name. When the chemical structure and chemical name conflict, the chemical structure is determinative of the identity of the compound. Compounds described herein may contain one or more chiral centers and/or double bonds and therefore, may exist as stereoisomers, such as double-bond isomers such as geometric isomers, enantiomers or diastereomers. Accordingly, the chemical structures depicted herein encompass all possible enantiomers and stereoisomers of the illustrated compounds including the stereoisomerically pure form (for example, geometrically pure, enantiomerically pure, or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds may exist in unsolvated forms as well as solvated forms, including hydrated forms and as N-oxides. In general, compounds may be hydrated, solvated, or N-oxides. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that an asterisk indicates the point of attachment of the partial structure to the rest of the molecule.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-10}$ cycloalkyl, and in certain embodiments a $C_{3-7}$ cycloalkyl.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutical composition" refers to at least one compound and at least one pharmaceutically acceptable vehicle, with which the compound is administered to a patient.

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and (2) salts formed when an acidic proton present in the parent compound is replaced by a metal ion, for example, an alkali metal ion, an alkaline earth ion, or an aluminum ion; or coordinates with an organic base such as ethanolamine, diethanolamine, triethanolamine, N-methylglucamine, and the like.

"Pharmaceutically acceptable vehicle" refers to a diluent, adjuvant, excipient or carrier with which a compound is administered.

"Patient" includes animals and mammals, for example humans.

"Preventing" or "prevention" refers to a reduction in risk of acquiring a disease or disorder, for example, causing at least one of the clinical symptoms of the disease not to develop in a patient that may be exposed to or predisposed to the disease but does not yet experience or display symptoms of the disease.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry," (Wiley, 2$^{nd}$ ed. 1991) and Harrison et al., "Compendium of Synthetic Organic Methods," Vols. 1–8 (John Wiley and Sons, 1971–1996). Examples of amino protecting groups include, but are not limited to, formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Examples of hydroxy protecting groups include, but are not limited to, those in which the hydroxy group is either acylated or alkylated such as benzyl, and trityl ethers as well as alkyl ethers, tetrahydropyranyl ethers, trialkylsilyl ethers, and allyl ethers.

"Solvate" refers to a molecular complex of a compound with one or more solvent molecules in a stoichiometric or non-stoichiometric amount. Such solvent molecules are those commonly used in the pharmaceutical art, which are known to be innocuous to a recipient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a complex where the one or more solvent molecules are water.

"Treating" or "treatment" of any disease or disorder refers, in some embodiments, to ameliorating the disease or disorder, for example, arresting or reducing the development of the disease or at least one of the clinical symptoms thereof. In certain embodiments "treating" or "treatment" refers to ameliorating at least one physical parameter, which may not be discernible by the patient. In certain embodiments, "treating" or "treatment" refers to inhibiting the disease or disorder, either physically, (e.g., stabilization of a discernible symptom), physiologically, for example, stabilization of a physical parameter, or both. In certain embodiments, "treating" or "treatment" refers to delaying the onset of the disease or disorder.

"Therapeutically effective amount" means the amount of a compound that, when administered to a patient for treating a disease is sufficient to effect such treatment for the disease. The "therapeutically effective amount" can vary depending on the compound, the disease and its severity, the age of the patient to be treated and/or the weight of the patient to be treated.

Reference is now be made in detail to embodiments of the present disclosure. While certain embodiments of the present disclosure are described, it will be understood that it is not intended to limit the embodiments of the present disclosure to those described herein. To the contrary, reference to embodiments of the present disclosure is intended to cover alternatives, modifications, and equivalents as may be included within the spirit and scope of the embodiments of the present disclosure by the appended claims.

Compounds

Certain embodiments of the present disclosure provide compounds of Formula (I):

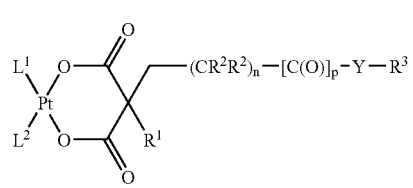

(I)

or a pharmaceutically acceptable salt thereof, or a pharmaceutically acceptable solvate of any of the foregoing, wherein:

n is an integer from 0 to 4;

p is chosen from 0 and 1;

$L^1$ and $L^2$ are each $NH_3$ or $L^1$ and $L^2$ together form a 1,2-cycloalkanediamine chosen from trans-(1R,2R)-cyclohexanediamine, trans-(1S,2S)-cyclohexanediamine, and cis-(R,S)-cyclohexanediamine;

$R^1$ is chosen from hydrogen and $C_{1-4}$ alkyl;

each $R^2$ is independently chosen from hydrogen and $C_{1-4}$ alkyl;

Y is chosen from —$NR^5$— and —O—;

$R^3$ is chosen from

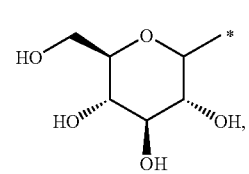

(II)

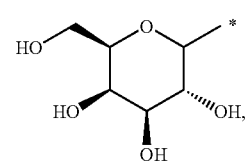

(III)

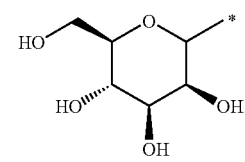

(IV)

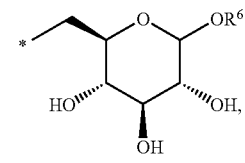

(V)

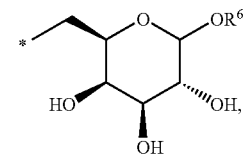

(VI)

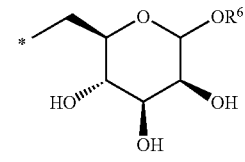

(VII)

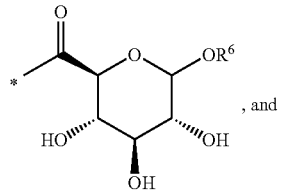

(VIII)

, and

-continued

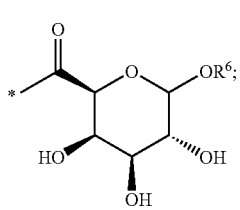
(IX)

wherein $R^6$ is chosen from hydrogen and $C_{1-4}$ alkyl; and $R^5$ is chosen from hydrogen and $C_{1-4}$ alkyl.

In certain embodiments of compounds of Formula (I), $R^1$ is hydrogen.

In certain embodiments of compounds of Formula (I), each $R^2$ is hydrogen.

In certain embodiments of compounds of Formula (I), n is chosen from 1 and 2.

In certain embodiments of compounds of Formula (I), Y is chosen from —NH— and and —O—.

In certain embodiments of compounds of Formula (I), $R^6$ is chosen from hydrogen and methyl.

In certain embodiments of compounds of Formula (I), $L^1$ and $L^2$ are each $NH_3$ or $L^1$ and $L^2$ together are trans-(1R,2R) cyclohexanediamine.

In certain embodiments of compounds of Formula (I), $L^1$ and $L^2$ together are trans-(1R,2R)-cyclohexanediamine.

In certain embodiments of compounds of Formula (I), $R^1$ is hydrogen and each $R^2$ is hydrogen.

In certain embodiments of compounds of Formula (I), $R^1$ is hydrogen, each $R^2$ is hydrogen, and n is chosen from 1 and 2.

In certain embodiments of compounds of Formula (I), $R^1$ is hydrogen, each $R^2$ is hydrogen, and Y is —NH—.

In certain embodiments of compounds of Formula (I), $R^1$ is hydrogen, each $R^2$ is hydrogen, n is chosen from 1 and 2, and Y is —NH—.

In certain embodiments of compounds of Formula (I), $R^1$ is hydrogen, each $R^2$ is hydrogen, n is chosen from 1 and 2, and Y is —O—.

Certain embodiments of the present disclosure provide compounds of Formula (X):

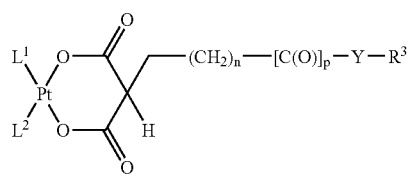
(X)

or a pharmaceutically acceptable salt thereof, or a pharmaceutically acceptable solvate of any of the foregoing, wherein:

n is chosen from 1 and 2;
p is chosen from 0 and 1;
$L^1$ and $L^2$ are each $NH_3$ or $L^1$ and $L^2$ together are trans-(1R,2R)-cyclohexanediamine;
Y is chosen from —NH— and —O—; and
$R^3$ is chosen from

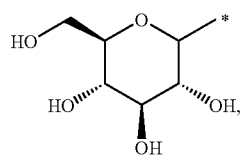
(II)

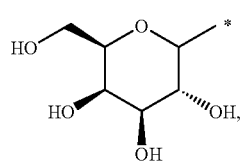
(III)

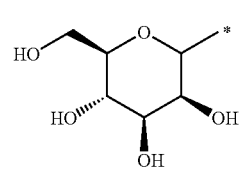
(IV)

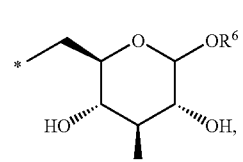
(V)

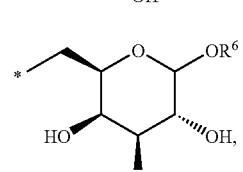
(VI)

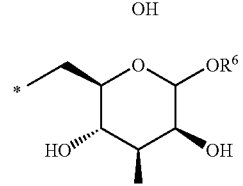
(VII)

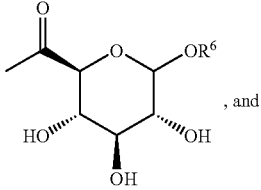
(VIII)
, and

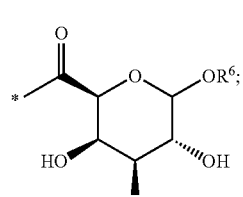
(IX)

wherein $R^6$ is chosen from hydrogen and methyl.

In certain embodiments of compounds of Formula (X), Y is —NH—.

In certain embodiments of compounds of Formula (X), Y is —O—.

Certain embodiments of the present disclosure provide a compound chosen from:

[1R,2R-Cyclohexanediamine-N, N'][{2-(β-D-Glucopyranos-1-ylamido)ethyl}propanedioato(2-)-O,O']Platinum (II);

[1R,2R-Cyclohexanediamine-N,N'][{2-(β-D-Galactopyranos-1-ylamido)ethyl}propanedioato(2-)-O,O']Platinum (II);

[1R,2R-Cyclohexanediamine-N,N'][{2-(β-D-Mannopyranos-1-ylamido)ethyl}propanedioato(2-)-O,O']Platinum (II);

[1R,2R-Cyclohexanediamine-N,N'][{3-(β-D-Glucopyranos-1-ylamido)propyl}propanedioato(2-)-O,O']Platinum (II);

[1R,2R-Cyclohexanediamine-N,N'][{3-(β-D-Galactopyranos-1-ylamido)propyl}propanedioato(2-)-O,O']Platinum (II);

[1R,2R-Cyclohexanediamine-N,N'][{3-(α,β-D-Galactopyranos-6-ylamido)propyl}propanedioato(2-)-O,O']Platinum(II);

[Diammine][{3-(α,β-D-Galactopyranos-6-ylamido)propyl}propanedioato(2-)-O,O']Platinum(II);

[1R,2R-Cyclohexanediamine-N,N'][{3-(α,β-D-Mannopyranos-6-ylamido)propyl}propanedioato(2-)-O,O']Platinum (II);

[1R,2R-Cyclohexanediamine-N,N'][{3-(α,β-D-Glucopyranos-6-ylamido)propyl}propanedioato(2-)-O,O']Platinum (II);

[1R,2R-Cyclohexanediamine-N,N'][{3-(Methyl-α-D-Glucopyranos-6-ylamido)propyl}propanedioato(2-)-O,O']Platinum(II);

[1R,2R-Cyclohexanediamine-N, N'][{2-(Methyl-(α-D-Glucopyranos-6-yl-carbonyl)ethyl}propanedioato(2-)-O,O']Platinum(II);

[1R,2R-Cyclohexanediamine-N,N'][{2-(Methyl-α-D-Mannopyranos-6-yl-carbonyl)ethyl}propanedioato(2-)-O,O']Platinum(II);

[1R,2R-Cyclohexanediamine-N,N'][{2-(α,β-D-Glucopyranos-1-yl)ethyl}propanedioato(2-)-O,O']Platinum(II);

[1R,2R-Cyclohexanediamine-N,N'][{2-(α,β-D-Galactopyranos-1-yl)ethyl}propanedioato(2-)-O,O']Platinum(II);

[1R,2R-Cyclohexanediamine-N,N'][{2-(α,β-D-Glucuron-6-yl-amido)ethyl}propanedioato(2-)-O,O']Platinum(II);

[1R,2R-Cyclohexanediamine-N,N'][{2-(α,β-D-Galacturon-6-yl-amido)ethyl}propanedioato(2-)-O,O']Platinum(II);

[1R,2R-Cyclohexanediamine-N,N'][{2-(Methyl-β-D-Glucuron-6-yl-amido)ethyl}propanedioato(2-)-O,O']Platinum(II); and

[1R,2R-Cyclohexanediamine-N,N'][{3-(α,β-D-Mannopyranos-1-yl)propyl}propanedioato(2-)-O,O']Platinum(II);

or a pharmaceutically acceptable salt thereof, or a pharmaceutically acceptable solvate of any of the foregoing.

Certain embodiments of the present disclosure provide compounds of Formula (XI):

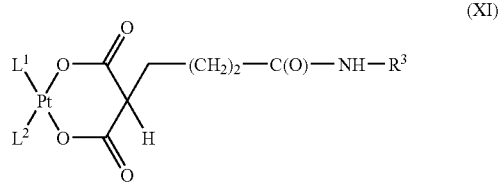

(XI)

or a pharmaceutically acceptable salt thereof, or a pharmaceutically acceptable solvate of any of the foregoing, wherein:

$L^1$ and $L^2$ are each $NH_3$ or $L^1$ and $L^2$ together form a 1,2-cycloalkanediamine chosen from trans-(1R,2R)-cyclohexanediamine, trans-(1S,2S)-cyclohexanediamine, and cis-(R,S)-cyclohexanediamine; and $R^3$ is

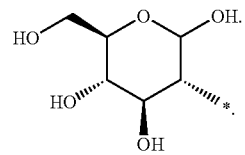

In certain embodiments of compounds of Formula (XI), $L^1$ and $L^2$ are each $NH_3$ or $L^1$ and $L^2$ together are trans-(1R, 2R)-cyclohexanediamine.

Certain embodiments of the present disclosure provide compounds chosen from [1R,2R-Cyclohexanediamine-N, N'][{3-(α,β-D-Glucopyranos-2-yl-amido)propyl}propanedioato(2-)-O,O']Platinum (II), and [Diammine][{3-(α,β-D-Glucopyranos-2-yl-amido)propyl}propanedioato(2-)-O,O']Platinum(II), or pharmaceutically acceptable salts thereof, or pharmaceutically acceptable solvates of any of the foregoing.

Synthesis of Certain Compounds

The compounds disclosed herein may be obtained via the synthetic methods illustrated in Schemes 1–5. General synthetic methods useful in the synthesis of the compounds described herein are available in the art (e.g., Green et al., "Protective Groups in Organic Chemistry," (Wiley, 2nd ed. 1991); Harrison et al., "Compendium of Synthetic Organic Methods," Vols. 1–8 (John Wiley and Sons, 1971–1996); Larock, "Comprehensive Organic Transformations," (VCH Publishers, 1989); and Paquette, "Encyclopedia of Reagents for Organic Synthesis," (John Wiley & Sons, 1995)).

Accordingly, starting materials useful for preparing compounds and intermediates thereof, and/or practicing methods disclosed herein are commercially available or can be prepared by well-known synthetic methods. Other methods for synthesis of the compounds disclosed herein are either described in the art or will be readily apparent to the skilled artisan in view of the references provided above and may be used to synthesize the compounds disclosed herein. Accordingly, the methods presented in the Schemes herein are illustrative rather than comprehensive. For example, one of ordinary skill will appreciate that the synthetic methods provided in Schemes 1–5 illustrate the preparation of platinum complexes containing the ligand trans-(1R,2R)-cyclohexanediamine from the precursor compound [trans-(1R, 2R)-cyclohexanediamine]-sulfato-platinum(II) (i.e., (DACH)PtSO$_4$). Accordingly one of ordinary skill will appreciate that other compounds of Formula (I) disclosed herein may be prepared analogously from [trans-(1S,2S)-cyclohexanediamine]-sulfato-platinum(II), [cis-(R,S)-cyclohexanediamine]-sulfato-platinum(II), or diamminesulfato-platinum(II). Moreover while the absolute and relative stereochemistry of substituents on the hexose moieties in Schemes 1–5 are not explicitly specified, one of ordinary skill will appreciate that these are apparent by reference to the structures of moieties of Formulae (II)–(IX) disclosed herein.

In certain embodiments, compound (9) (viz. a compound of Formula (I) wherein $L^1$ and $L^2$ together are trans-(1R, 2R)-cyclohexanediamine, $R^1$ is hydrogen, $R^2$ is hydrogen, n and p are each 1, $R^3$ is a moiety of Formulae (II)–(IV), Y is $NR^5$ and $R^5$ is hydrogen) may be synthesized as illustrated in Scheme 1. The protected malonic acid derivative (4) is converted to an activated ester such as (5) and used to acylate amino sugar (6). Deprotection of the resulting compound (7) affords malonate ligand (8), which after conversion to its barium salt is reacted with the platinum sulfato complex $(DACH)PtSO_4$ to provide target compound (9).

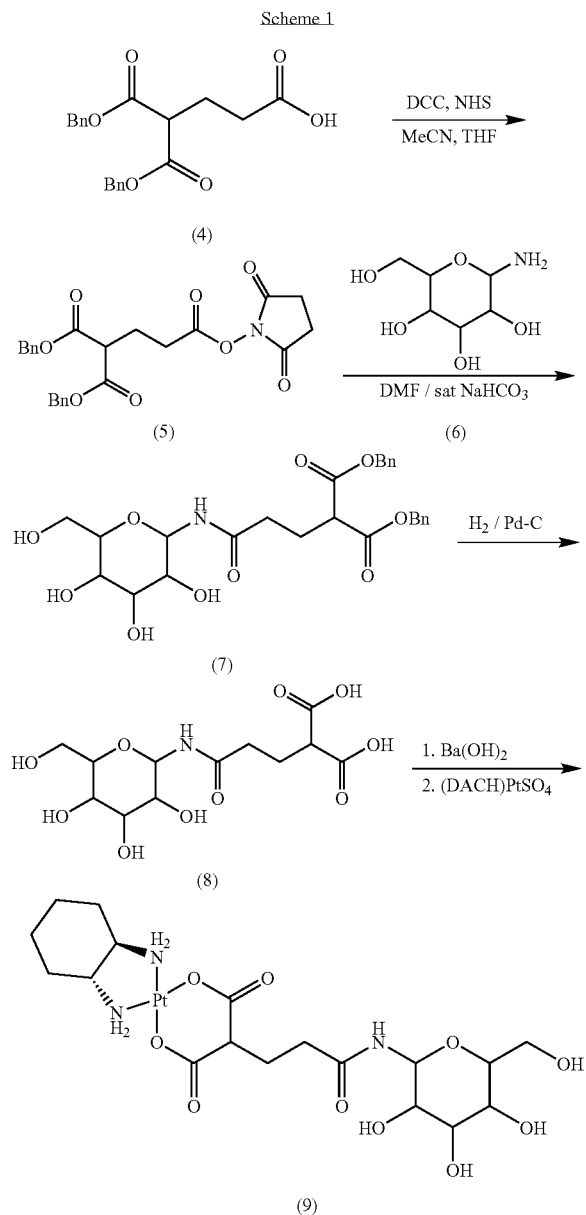

In certain embodiments, compound (14) (viz. a compound of Formula (I) wherein $L^1$ and $L^2$ together are trans-(1R, 2R)-cyclohexanediamine, $R^1$ is hydrogen, $R^2$ is hydrogen, n and p are each 1, $R^3$ is a moiety of Formulae (V)–(VII), Y is $NR^5$, $R^5$ is hydrogen, and $R^6$ is hydrogen) may be synthesized as illustrated in Scheme 2. Acylation of the 6-amino sugar (10) with activated ester (5), then deprotection of the resulting methyl glycoside (11) in two steps affords malonate ligand (13), which after conversion to its barium salt is reacted with the platinum sulfato complex $(DACH)PtSO_4$ to provide target compound (14).

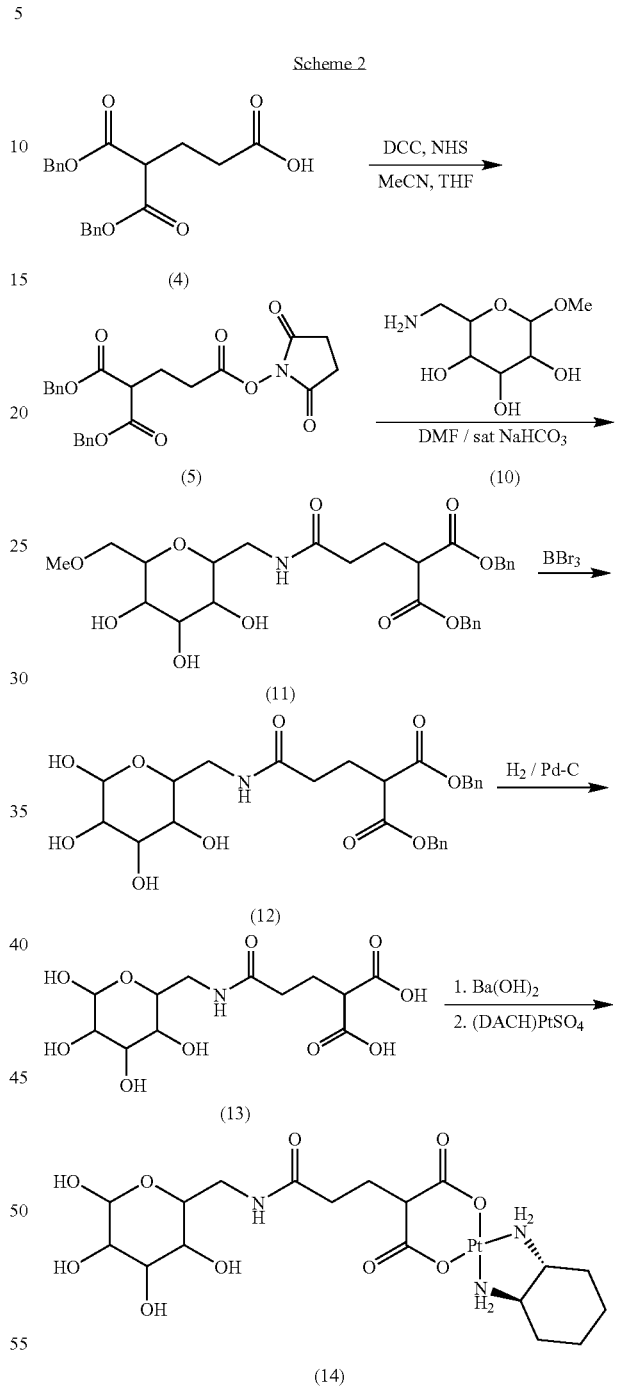

In certain embodiments, compound (20) (viz. a compound of Formula (I) wherein $L^1$ and $L^2$ together are trans-(1R, 2R)-cyclohexanediamine, $R^1$ is hydrogen, $R^2$ is hydrogen, p is 0, n is 1, $R^3$ is a moiety of Formulae (VIII) or (IX), Y is $NR^5$, $R^5$ is hydrogen and $R^6$ is hydrogen) may be synthesized as illustrated in Scheme 3. The protected glycuronic acid derivative (15) is converted to an activated ester such as (16) and used to acylate protected aminomalonate compound (17). Deprotection of the resulting compound (18) in two steps affords malonate ligand (19), which after conversion to its barium salt is reacted with the platinum sulfato complex (DACH)PtSO$_4$ to provide target compound (20).

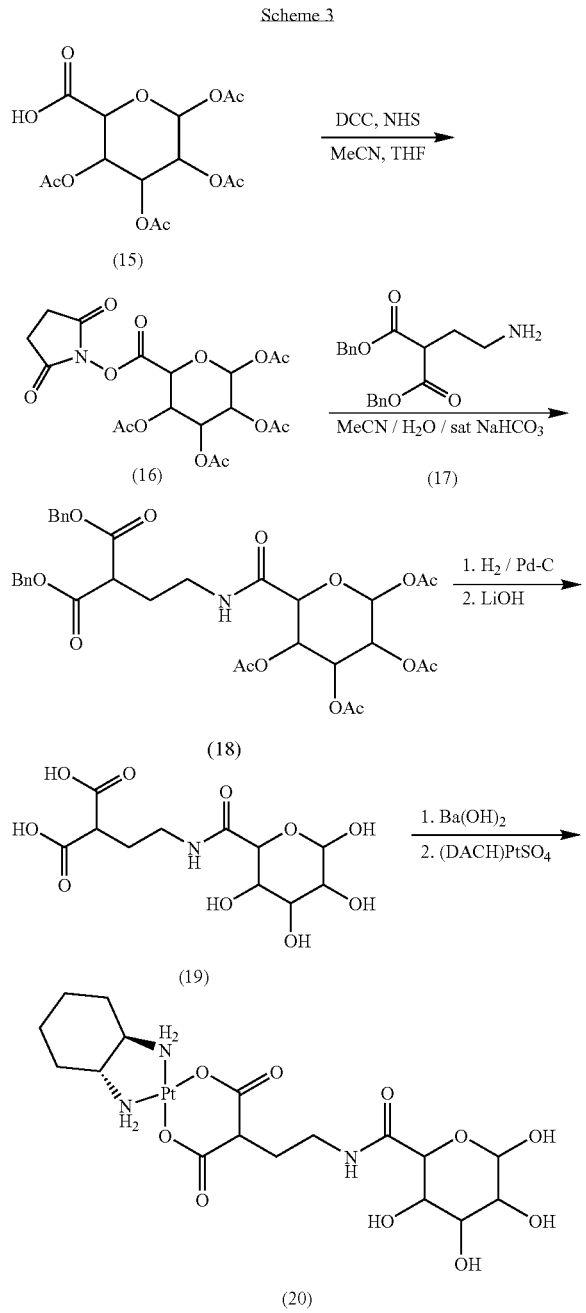

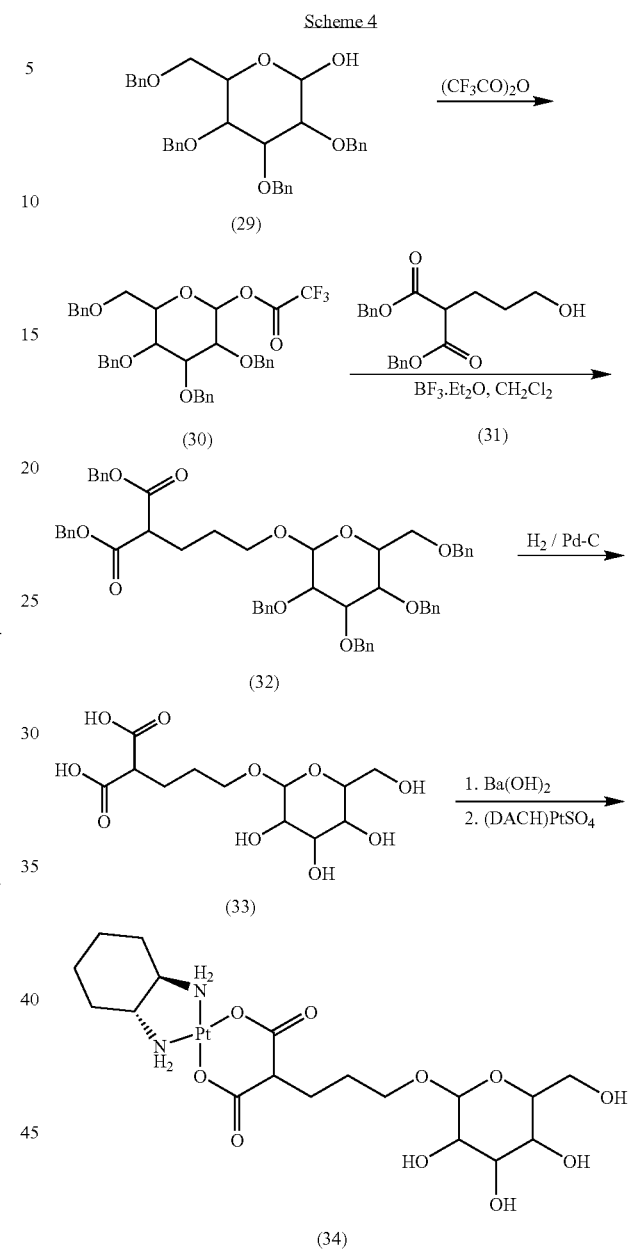

In certain embodiments, compound (34) (viz. a compound of Formula (1) wherein L$^1$ and L$^2$ together are trans-(1R, 2R)-cyclohexanediamine, R$^1$ is hydrogen, R$^2$ is hydrogen, p is 0, n is 2, R$^3$ is a moiety of Formulae (II)–(IV), and Y is 0) may be synthesized as illustrated in Scheme 4. Activation of the protected sugar (29) via trifluoroacetylation followed by reaction with alcohol (31) provides compound (32), which upon deprotection affords malonate ligand (33), which is further converted via its barium salt through reaction with the platinum sulfato complex (DACH)PtSO$_4$ to provide target compound (34).

An alternative synthesis of compound (34) is outlined in Scheme 5, wherein dibenzylmalonate is alkylated with the sugar bromide (36), prepared, for example, by reacting 3-bromopropanol (35) with compound (30) to provide compound (32), which is further elaborated to provide compound (34) as disclosed in Scheme 4.

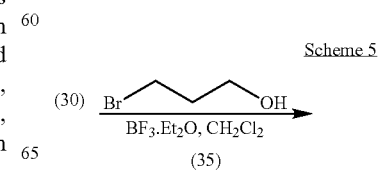

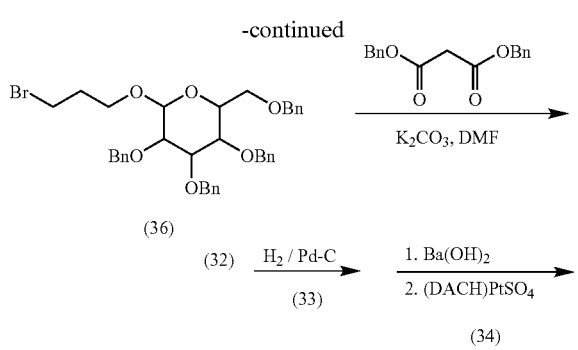

Pharmaceutical Compositions

Pharmaceutical compositions comprising a therapeutically effective amount of one or more platinum-containing compounds of Formulae (I), (X), or (XI), preferably in purified form, together with a suitable amount of a pharmaceutically acceptable vehicle, so as to provide a form for proper administration to a patient are provided herein. Suitable pharmaceutical vehicles include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents. In addition, auxiliary, stabilizing, thickening, lubricating, and coloring agents may be used.

Pharmaceutical compositions may be manufactured by means of conventional mixing, dissolving, granulating, dragee-making, levigating, emulsifying, encapsulating, entrapping, or lyophilizing processes. Pharmaceutical compositions may be formulated in conventional manner using one or more physiologically acceptable carriers, diluents, excipients or auxiliaries, which facilitate processing of compounds disclosed herein into preparations which can be used pharmaceutically. Proper formulation is dependent upon the route of administration chosen.

Pharmaceutical compositions can be administered topically, orally, intranasally, intradermally, subcutaneously, intrathecally, intramuscularly, topically, intravenously, or injected directly to a site of cancerous tissue.

A pharmaceutical composition can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 19th Edition, 1995). In some embodiments, compositions are formulated for oral delivery, particularly for oral sustained release administration.

Pharmaceutical compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, when in tablet or pill form, the compositions may be coated to delay disintegration and absorption in the gastrointestinal tract, thereby providing a sustained action over an extended period of time. Oral compositions can include standard vehicles such as mannitol, lactose, starch, magnesium stearate, sodium saccharine, cellulose, magnesium carbonate, and the like. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines, and the like may be added.

When a compound of Formula (I), (X), or (XI) is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases, and tend to be more soluble in aqueous and other protic solvents than the corresponding free acid form. In some embodiments, sodium salts of a compound of Formulae (I), (X), or (XI) are used in the above described formulations.

Sustained Release Dosage Forms

Platinum-containing compounds and compositions thereof of the present disclosure can be practiced with a number of different dosage forms, which can be adapted to provide sustained release of compounds of Formulae (I), (X), or (XI) upon oral administration.

In certain embodiments, the dosage form can comprise beads that on dissolution or diffusion release the compound over an extended period of hours, in some embodiments, over a period of at least 4 hours, in some embodiments, over a period of at least 8 hours, over a period of at least 12 hours, over a period of at least 24 hours, and in other embodiments, over a period of more than 24 hours. The platinum-containing compound-releasing beads can have a central composition or core comprising a platinum-containing compound and pharmaceutically acceptable vehicles, including an optional lubricant, antioxidant, and/or buffer. Suitable timed-release beads are disclosed in Lu, *Int. J. Pharm.*, 1994, 112, 117–124; Pharmaceutical Sciences by Remington, 14th ed, pp. 1626–1628 (1970); Fincher, *J. Pharm. Sci.*, 1968, 57, 1825–1835; and U.S. Pat. No. 4,083,949). Suitable tablets are disclosed in Pharmaceutical Sciences by Remington, 17th Ed, Ch. 90, 1603–1625 (1985).

In certain embodiments, an oral sustained release pump can be used (see Langer, *Science*, 1990, 249,1527–1533; Sefton, *CRC Crit. Ref. Biomed. Eng.*, 1987, 14, 201; and Saudek et al., *N. Engl. J. Med.*, 1989, 321, 574).

In certain embodiments, polymeric materials can be used for oral sustained release delivery such as described, for example, in "Medical Applications of Controlled Release," Langer and Wise (eds.), CRC Press, Boca Raton, Fla. (1974); "Controlled Drug Bioavailability," Drug Product Design and Performance, Smolen and Ball (eds.), Wiley, New York (1984); Langer et al., *J. Macromol. Sci. Rev. Macromol Chem.*, 1983, 23, 61; Levy et al., *Science*, 1985, 228: 190; During et al., *Ann. Neurol.*, 1989, 25, 351; and Howard et al., *J. Neurosurg.*, 1989, 71, 105.

In certain embodiments, enteric-coated preparations can be used for oral sustained release administration. In certain embodiments, coating materials include polymers with a pH-dependent solubility (i.e., pH-controlled release), polymers with a slow or pH-dependent rate of swelling, dissolution or erosion (i.e., time-controlled release), polymers that can be degraded by enzymes (i.e., enzyme-controlled release) and polymers that form firm layers that can be destroyed by an increase in pressure (i.e., pressure-controlled release).

In certain embodiments, drug-releasing lipid matrices or drug-releasing waxes can be used for oral sustained release administration.

In certain embodiments, a controlled-release system can be placed in proximity to the target of the compound, thus requiring only a fraction of the systemic dose (see Goodson, in "Medical Applications of Controlled Release," supra, vol. 2, pp. 115–138 (1984)). Other controlled-release systems discussed in Langer, *Science,* 1990, 249, 1527–1533 can also be used.

In certain embodiments, a dosage form can comprise a platinum-containing compound coated on a polymer substrate. The polymer can be an erodible, or a nonerodible polymer. Representative biodegradable polymers are described, for example, in Rosoff, Controlled Release of Drugs, Chap. 2, 53–95 (1989); and in U.S. Pat. Nos. 3,811,444; 3,962,414; 4,066,747; 4,070,347; 4,079,038; and 4,093,709.

In certain embodiments, a dosage form can comprise a compound loaded into a polymer that releases the compound by diffusion through a polymer, or by flux through pores or by rupture of a polymer matrix as described, for example, in Coleman et al., *Polymers,* 1990, 31, 1187–1231; Roerdink et al., *Drug Carrier Systems,* 1989, 9, 57–100; Leong et al., *Adv. Drug Delivery Rev.,* 1987, 1, 199–233; Roff et al., Handbook of Common Polymers, 1971, CRC Press; and U.S. Pat. No. 3,992,518.

In certain embodiments, a dosage from can comprise a plurality of pills. The time-release pills can provide a number of individual doses for providing various time doses for achieving a sustained release compound delivery profile over an extended period of time.

In certain embodiments, osmotic delivery systems can be used for oral sustained release administration (see Verma et al., *Drug Dev. Ind. Pharm.,* 2000, 26, 695–708).

Regardless of the specific form of sustained release oral dosage form used, a platinum-containing compound of the present disclosure can be released from the dosage form, such as an orally administered dosage form, over a sufficient period of time to provide prolonged therapeutic concentrations of the platinum-containing compound in the plasma and/or blood of a patient enabling administration of the dosage form on only a once or twice per day basis. In certain embodiments, a therapeutic or prophylactic plasma and/or blood concentration of a platinum-containing compound can be maintained in the systemic circulation of an animal following oral administration of the platinum-containing compound over a period of at least 4 hours, in certain embodiments, over a period of at least 8 hours, and in certain embodiments, over a period of at least 12 hours.

Doses

Platinum-containing compounds of the present disclosure can be administered to treat or prevent diseases or disorders such as cancer.

The amount of platinum-containing compound that will be effective in the treatment of a particular disorder or condition can depend on the nature of the disorder or condition, and can be determined by standard clinical techniques known in the art. In addition, in vitro or in vivo assays may optionally be employed to help identify optimal dosage ranges. The amount of a compound administered will, of course, depend on, among other factors, the subject being treated, the weight of the subject, the severity of the affliction, the manner of administration and the judgment of the prescribing physician.

In certain embodiments, a dosage form can be adapted to be administered to a patient no more than twice per day, and in certain embodiments, only once per day. Dosing may be provided alone or in combination with other drugs and may continue as long as required for effective treatment of the disease state or disorder. In certain embodiments, a platinum-containing compound of the present disclosure can be administered continuously over a period of hours, such as when administered intravenously.

Suitable dosage ranges for oral administration can depend on the potency of the platinum-containing compound. For certain platinum-containing compounds, a dose can be equitoxic to a dose of oxaliplatin ranging from about 0.1 mg to about 50 mg per kilogram body weight, from about 0.5 mg to about 30 mg per kilogram body weight, and in certain embodiments from about 1 to about 20 mg per kilogram body weight. Certain platinum-containing compounds may be more or less potent and lower or higher doses may be appropriate. Dosage ranges and regimens can be selected to be therapeutically effective for treating cancer in a patient. Dosage ranges and regimens may be readily determined by methods known to the skilled artisan.

Uses of Compounds, Compositions and Dosage Forms

In some embodiments, a therapeutically effective amount of one or more compounds of Formulae (I), (X), and/or (XI) can be administered to a patient, such as a human, suffering from cancer.

Compounds of Formulae (I), (X), and (XI) and pharmaceutical compositions disclosed herein can be used in methods of treating cancer. Examples of tumors amenable to treatment are cancers of the bladder, brain, breast, colon, esophagus, kidney, leukemia, liver, lung, oral cavity, ovary, pancreas, prostate, skin, stomach, and uterus. In certain embodiments, compounds and compositions can be used for treating solid tumors, such as sarcoma, lymphomas, and carcinomas. In certain embodiments, compounds and compositions can be used in treating cancers in which expression of one or more GLUT transporters, such as GLUT1, GLUT3, and/or GLUT5 is higher in the cancer than in normal cells from the same noncarcinogenic tissue. Examples of these cancers include brain cancers, such as astrocytoma, glioblastoma multiforme, malignant ependymana, and medullablastoma. Breast cancers amenable to treatment include infiltrating ductal adenocarcinoma, ductal adenocarcinoma, and lobular adenocarcinoma. Lung cancers amenable to treatment include squamous cell carcinoma, and epidermoid carcinoma. Colon cancers amenable to treatment include colon adenocarcinoma, medullary carcinoma and mucinous carcinoma. Prostate cancers amenable to treatment include prostate sarcoma. Incorporation of isotopes such as boron ($^{10}$B) allows boron neutron capture therapies (BNCT) in which low-energy neutron irradiation is used to induce boron decay and release of higher energy particles that are toxic to cells. An advantage of this and similar approaches relative to existing chemotherapy approaches is that release of particles from decaying isotopes can kill neighboring cells as well, and provide more complete tumor killing in poorly vascularized solid tumors. Another advantage of these approaches is that tumors in highly radiation sensitive tissues (liver, pancreas) can be targeted.

In certain embodiments, a therapeutically effective amount of one or more compounds of Formulae (I), (X), and/or (XI) can be administered to a patient, such as a human, as a preventative measure against various diseases or disorders. Thus, the therapeutically effective amount of one or more compounds of Formulae (I), (X), and/or (XI) can be administered as a preventative measure to a patient having a predisposition for cancer.

In prophylactic applications, pharmaceutical compositions can be administered to a patient susceptible to, or otherwise at risk of, cancer in an amount and frequency sufficient to eliminate or reduce the risk, lessen the severity, or delay the outset of the disease, including biochemical, histologic, and/or behavioral symptoms of the disease, its complications and intermediate pathological phenotypes presenting during development of the disease. In therapeutic applications, pharmaceutical compositions can be administered to a patient suspected of, or already suffering from such a disease in an amount and frequency sufficient to cure, or at least partially arrest, the symptoms of the disease (biochemical, histologic, and/or behavioral), including its complications and intermediate pathological phenotypes in development of the disease. An amount of pharmaceutical composition sufficient to achieve at least one of the above objects is referred to as an effective amount, and a combination of amount and frequency sufficient to achieve at least one of the above objects is referred to as an effective regimen.

Optionally, administration of a pharmaceutical composition can be combined with administration of a second chemotherapeutic agent and/or radiation. When used to treat or prevent cancer a therapeutically effective amount of one or more compounds of Formulae (I), (X), and/or (XI) may be administered or applied singly, or in combination with other agents. A therapeutically effective amount of one or more compounds of Formulae (I), (X), and/or (XI) may also deliver a compound disclosed herein in combination with another pharmaceutically active agent, including another compound disclosed herein. For example, in the treatment of a patient suffering from cancer, a dosage form comprising a compound of Formulae (I), (X), and/or (XI) may be administered in conjunction with a second active agent, which can be useful for treating cancer. Treatment with the second active agent may be prior to, concomitant with, or following treatment with a compound of Formulae (I), (X), and/or (XI). In certain embodiments, a compound of Formulae (I), (X), and/or (XI) can be combined with another active agent in a single dosage form. Examples of suitable antitumor therapeutics that may be used in combination with a compound of the present disclosure include, but are not limited to, chemotherapeutic agents, such as for example mitomycin C, taxol, paclitaxel, etoposide, 5-fluorouracil, and doxorubicin. Radiotherapeutic antitumor agents can also be used, alone or in combination with chemotherapeutic agents.

Compounds of the present disclosure can be used to inhibit cell growth in vitro or in vivo. Cell growth can be inhibited by contacting a cell with an effective amount of at least one compound of the present disclosure. For in vivo applications cell growth can be inhibited by administering to a mammal an effective amount of a compound of the present disclosure by any appropriate method such as any of those disclosed herein. In certain embodiments, the cell can be a cancer cell such as any of those disclosed herein.

EXAMPLES

The following examples describe in detail preparation of compounds and compositions disclosed herein and assays for using compounds and compositions disclosed herein. It will be apparent to those of ordinary skill in the art that many modifications, both to materials and methods, may be practiced.

In the examples below, the following abbreviations have the following meanings. If an abbreviation is not defined, it has its generally accepted meaning.

| | |
|---|---|
| Boc = | tert-butyloxycarbonyl |
| Cbz = | carbobenzyloxy |
| DCC = | dicyclohexylcarbodiimide |
| DMAP = | 4-N,N-dimethylaminopyridine |
| DMEM = | Dulbecco's Modified Eagle Medium |
| DMF = | N,N-dimethylformamide |
| DMSO = | dimethylsulfoxide |
| eq = | equivalents |
| FBS = | fetal bovine serum |
| g = | gram |
| h = | hour |
| HPLC = | high pressure liquid chromatography |
| kg = | killogram |
| L = | liter |
| LC/MS = | liquid chromatography/mass spectroscopy |
| M = | molar |
| m =g | milligram |
| min = | minute |
| mL = | milliliter |
| mmol = | millimoles |
| N = | normal |
| r.t. = | room temperature |
| THF = | tetrahydrofuran |
| TFA = | trifluoroacetic acid |
| TLC = | thin layer chromatography |
| TMS = | trimethylsilyl |
| µL = | microliter |
| µM = | micromolar |
| v/v = | volume to volume |

General Experimental Procedures

In the examples illustrated below, the compounds were purified either by thin layer chromatography on silica gel plates or by preparative HPLC and analyzed by $^1$H NMR and LC/MS. Preparative HPLC for platinum compound purification was performed with a Waters 2487 HPLC system using a 25×2.1 cm Phenomenex Luna 5 µm $C_{18}$ column with mobile phase mixture of methanol and water. NMR spectra were recorded on a Varian AS400/54 spectrometer. LC/MS were performed using Alliance HT Waters 2790 and Waters Micromass ZQ system. Compounds of Formula (I) prepared herein are listed in Table 1 below.

TABLE 1
Specific Embodiments of Compounds of Formula (I) and (XI)
| Cmpd | L¹/L² | R¹ | R² | n | p | Y | R⁶ | R³ |
|---|---|---|---|---|---|---|---|---|
| (39) | (1R, 2R)-Diamino-cyclohexane | H | H | 1 | 1 | NH | — | 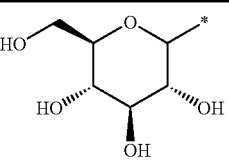 |
| (48) | (1R, 2R)-Diamino-cyclohexane | H | H | 2 | 1 | NH | — | 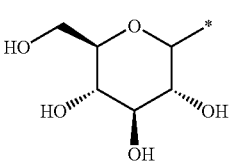 |
| (88) | (1R, 2R)-Diamino-cyclohexane | H | H | 1 | 0 | O | — | 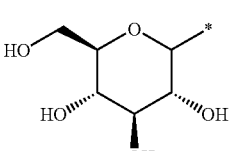 |
| (42) | (1R, 2R)-Diamino-cyclohexane | H | H | 1 | 1 | NH | — | 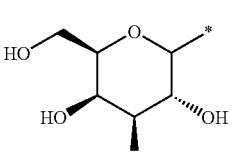 |
| (51) | (1R, 2R)-Diamino-cyclohexane | H | H | 2 | 1 | NH | — | 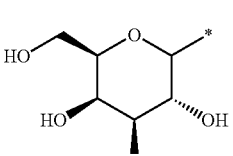 |
| (93) | (1R, 2R)-Diamino-cyclohexane | H | H | 1 | 0 | O | — | 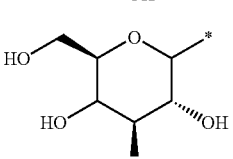 |
| (45) | (1R, 2R)-Diamino-cyclohexane | H | H | 1 | 1 | NH | — | 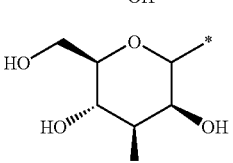 |
| (83) | (1R, 2R)-Diamino-cyclohexane | H | H | 2 | 0 | O | — | 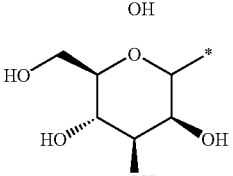 |
| (68) | (1R, 2R)-Diamino-cyclohexane | H | H | 1 | 1 | O | Me | 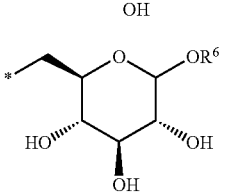 |

TABLE 1-continued
Specific Embodiments of Compounds of Formula (I) and (XI)
| Cmpd | L¹/L² | R¹ | R² | n | p | Y | R⁶ | R³ |
|------|-------|----|----|---|---|---|----|----|
| (66) | (1R, 2R)-Diamino-cyclohexane | H | H | 2 | 1 | NH | H | 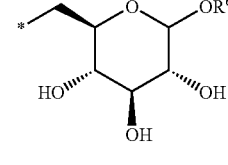 |
| (67) | (1R, 2R)-Diamino-cyclohexane | H | H | 2 | 1 | NH | Me | 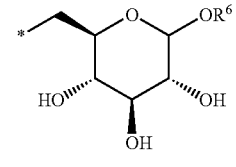 |
| (54) | (1R, 2R)-Diamino-cyclohexane | H | H | 2 | 1 | NH | H | 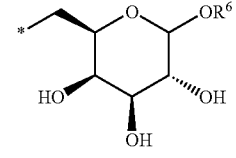 |
| (60) | Diammine | H | H | 2 | 1 | NH | H | 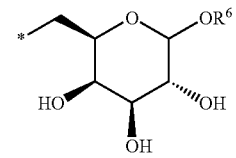 |
| (71) | (1R, 2R)-Diamino-cyclohexane | H | H | 1 | 1 | O | Me | 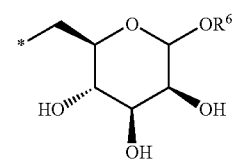 |
| (61) | (1R, 2R)-Diamino-cyclohexane | H | H | 2 | 1 | NH | H | 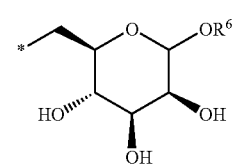 |
| (74) | (1R, 2R)-Diamino-cyclohexane | H | H | 1 | 0 | NH | H | 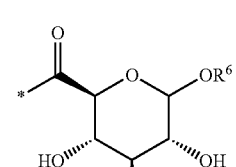 |
| (78) | (1R, 2R)-Diamino-cyclohexane | H | H | 1 | 0 | NH | Me | 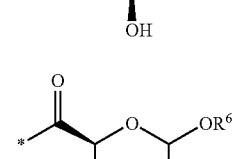 |

TABLE 1-continued

Specific Embodiments of Compounds of Formula (I) and (XI)

| Cmpd | $L^1/L^2$ | $R^1$ | $R^2$ | n | p | Y | $R^6$ | $R^3$ |
|---|---|---|---|---|---|---|---|---|
| (77) | (1R, 2R)-Diamino-cyclohexane | H | H | 1 | 0 | NH | H | (pyranose with C(O)* group, OR⁶, OH, OH, HO) |
| (79) | (1R, 2R)-Diamino-cyclohexane | H | H | 2 | 1 | NH | H | (pyranose with CH₂OH, OR⁶, OH, OH, * linkage) |
| (82) | Diammine | H | H | 2 | 1 | NH | H | (pyranose with CH₂OH, OR⁶, OH, OH, * linkage) |

Example 1

General Method for Preparation of [1R,2R-Cyclohexanediamine-N,N'][Propanediato-(2-)-O,O']Platinum(II) Complexes of Formula (I)

The appropriate malonic acid ligand (1 mmol) was dissolved in distilled water (10 mL) and a freshly prepared solution of Ba(OH)$_2$.8H$_2$O (1 mmol) in distilled water (2 mL) was added dropwise to this solution. After stirring for 15 min at room temperature a solution of cis-sulfato-[1R, 2R-cyclohexanediamine]platinum (II) (1 mmol) (i.e., (DACH)PtSO$_4$, prepared as described in *Analytica Chimica Acta,* 1991, 179, 281) in distilled water (2 mL) was added. The mixture was stirred overnight at room temperature and the resulting precipitate was removed by filtration. The filtrate was concentrated under vacuum at 40° C. and the product was purified by preparative HPLC using MeOH and H$_2$O as mobile phase provided the title compounds.

Example 2

General Method for Preparation of [Diammine][Propanediato-(2-)-O,O']Platinum (II) Complexes of Formula (I)

Following the method of Example 1 and replacing cis-sulfato-[1R,2R-cyclohexanediamine]platinum(II) with cis-sulfato-[diammine]platinum(II) provided the title compound.

Example 3

Dibenzyl (3-Carboxypropyl)propanedioate (37)

tert-Butyl-4-bromobutyrate (10 mmol) in DMF (100 mL) was treated with dibenzyl malonate (20 mmol) and potassium carbonate (30 mmol) at 40° C. overnight. EtOAc (200 mL) and saturated aqueous ammonium chloride (100 mL) were added and the separated organic layer was washed with 1N HCl (50 mL), saturated aqueous ammonium chloride (100 mL), brine (100 mL), and water (100 mL). After removal of the solvent in vacuo, the crude product was dissolved in dichloromethane (60 mL) and treated at room temperature with trifluoroacetic acid (15 mL) for 2 h. Removal of the solvent in vacuo afforded the crude product, which was purified by reverse phase preparative HPLC using 0.05% TFA/CH$_3$CN/H$_2$O as the mobile phase. The title compound (37) (2 g) was obtained as a colorless oil. $^1$H NMR (CD$_3$OD, 400 MHz): δ 7.3 (m, 10H), 5.1 (q, 4H), 3.5 (t, 1H), 2.3 (t, 2H), 1.9 (q, 2H), 1.6 (m, 2H). MS (ESI) m/z 370.4 (M+H)$^+$.

Example 4

Dibenzyl [3-(N-Succinimidyloxycarbonyl)propyl]propanedioate (38)

A solution of compound (37) (1.35 mmol) in CH$_3$CN (5 mL) and THF (5 mL) was treated with N-hydroxysuccinimide (2.02 mmol) and DCC (2.02 mmol). The reaction mixture was stirred at room temperature overnight. After removal of the precipitate by filtration and concentration of the filtrate in vacuo, the title compound (38) was obtained as a white solid and was used for coupling to an appropriate amino sugar without further purification.

Example 5

Dibenzyl(2-Carboxyethyl)propanedioate (4)

Following the method of Example 3 and replacing tert-butyl-4-bromobutyrate with tert-butyl-3-bromopropionate provided the title compound (4) (2 g) as a colorless oil. $^1$H NMR (CD$_3$CN, 400 MHz): δ 7.39 (m, 10H), 5.12–5.2 (m, 4H), 3.63 (t, 1H), 2.4 (t, 2H), 2.17 (m, 2H). MS (ESI) m/z 357.3 (M+H)$^+$.

Example 6

Dibenzyl[2-(N-Succinimidyloxycarbonyl)ethyl]propanedioate (5)

Following the method of Example 4 and replacing compound (37) with compound (4) provided the title compound (5) as a white solid.

Example 7

[1R,2R-Cyclohexanediamine-N,N'][{2-(β-D-Glucopyranos-1-ylamido)ethyl}propanedioato(2-)-O,O'] Platinum(II) (39)

Step A: Dibenzyl{2-(β-D-Glucopyranos-1-ylamido) ethyl}propanedioate (40)

Compound (5) (5.4 mmol) was dissolved in DMF (30 mL) and 1-amino-1-deoxy-β-D-glucopyranose (11 mmol) was added and the reaction mixture was stirred for 5 h at r.t. The reaction mixture was concentrated in vacuo and the residue purified by preparative reverse phase HPLC to afford the title compound (40) in 30–40% yield as a colorless oil. $^1$H NMR (CD$_3$CN, 400 MHz): δ 7.3 (m, 10H), 5.08–5.18 (q, 4H, J=12.4 Hz), 4.83 (d, 1H, J=9.2 Hz), 3.73 (dd, 1H), 3.57 (m, 2H), 3.39 (m, 1H), 3.35 (m, 1H), 3.2 (m, 2H), 2.3 (m, 2H), 2.15 (q, 2H). MS (ESI) m/z 518.36 (M+H)$^+$.

Step B: {2-(β-D-Glucopyranos-1-ylamido) ethyl}propanedioic Acid (41)

Compound (40) (0.40 mmol) was stirred with Pd—C (10% w/w) in a solution of ethyl acetate, ethanol, and water (1:1:0.25 v:v:v) (23 mL) under hydrogen atmosphere at room temperature for 4–8 h. The reaction mixture was filtered through a celite pad and washed successively with ethyl acetate (20 mL) and water (30 mL). The combined filtrate was concentrated in vacuo and lyophilized to give the title compound (41) as a colorless solid in quantitative yield. $^1$H NMR (D$_2$O, 400 MHz): δ 4.83 (d, 1H, J=9.2 Hz), 3.71–3.75 (dd, 1H, J=2.4, 2.0 Hz), 3.6 (dd, 1H, J=5.2, 5.6 Hz), 3.37–3.4 (m, 3H), 3.5 (q, 1H), 3.2 (m, 2H), 2.3 (m, 2H), 2.05 (m, 2H). MS (ESI) m/z: 338.26 (M+H)$^+$.

Step C: [1R,2R-Cyclohexanediamine-N,N'][{2-(β-D-Glucopyranos-1-ylamido)ethyl}propanedioato (2-)-O,O']Platinum(II) (39)

Following the method of Example 1 using compound (41) provided the title compound (39) (0.39 g, 67%) as a white solid. $^1$H NMR (D$_2$O, 400 MHz): δ 4.97 (d, J=8.8 Hz), 3.84–3.98 (m, 2H), 3.71 (dd, 1H, J=5.2, 12.4 Hz), 3.50–3.58 (m, 2H), 3.30–3.45 (m, 2H), 2.42–2.56 (m, 4H), 2.32–2.44 (m, 2H), 1.96–2.30 (m, 2H), 1.48–1.60 (m, 2H), 1.18–1.32 (m, 2H), 1.04–1.28 (m, 2H). MS (ESI) m/z: 644.32, 645.34, 646.42 main isotopes.

Example 8

[1R,2R-Cyclohexanediamine-N,N'][{2-(β-D-Galactopyranos-1-ylamido)ethyl}propanedioato(2-)-O,O'] Platinum(II) (42)

Step A: Dibenzyl{2-(β-D-Galactopyranos-1-ylamido)ethyl}propanedioate (43)

Following the method of Example 7, Step A and replacing 1-amino-1-deoxy-β-D-glucopyranose with 1-amino-1-deoxy-β-D-galactopyranose afforded the title compound (43). $^1$H NMR (CD$_3$CN, 400 MHz): δ 7.3 (m, 10H), 5.08–5.18 (q, 4H, J=12.4 Hz), 4.83 (d, 1H, J=9.2 Hz), 3.73 (m, 1H), 3.57 (m, 2H), 3.39 (m, 1H), 3.3 (m, 1H), 3.2 (m, 2H), 2.3 (m, 2H), 2.15 (q, 2H). MS (ESI) m/z: 518.36 (M+H)$^+$.

Step B: {2-(β-D-Galactopyranos-1-ylamido) ethyl}propanedioic Acid (44)

Following the method of Example 7, Step B and replacing compound (40) with compound (43) afforded the title compound (44). $^1$H NMR (D$_2$O, 400 MHz): δ 4.76 (d, 1H, J=8.8 Hz), 3.82 (d, 1H, J=3.6 Hz), 3.62 (m, 1H), 3.57 (m, 3H), 3.48 (q, 1H), 3.36 (t, 1H), 2.29 (m, 2H), 2.04 (m, 2H). MS (ESI) m/z: 338.3 (M+H)$^+$.

Step C: [1R,2R-Cyclohexanediamine-N,N'][{2-(β-D-Galactopyranos-1-ylamido)ethyl}propanedioato (2-)-O,O']Platinum(II) (42)

Following the method of Example 1 using compound (44) provided the title compound (42) (0.15 g, 65%) as a white solid. $^1$H NMR (D$_2$O, 400 MHz): δ 4.92 (d, J=8.8 Hz), 3.86–3.98 (m, 2H), 3.76 (q, 1H, J=6.4 Hz), 3.65–3.74 (m, 3H), 3.61 (t, 1H, J=9.2 Hz), 2.40–2.60 (m, 4H), 2.25–2.40 (m, 2H), 2.00 (d, 2H, J=11.6 Hz), 1.53 (d, 2H, J=9.2 Hz), 1.18–1.34 (m,2H), 1.00–1.18 (m, 2H). MS (ESI) m/z: 644.39, 645.40, 647.37 main isotopes.

Example 9

[1R,2R-Cyclohexanediamine-N,N'][{2-(β-D-Mannopyranos-1-ylamido)ethyl}propanedioato(2-)-O,O'] Platinum(II) (45)

Step A: Dibenzyl {2-(β-D-Mannopyranos-1-ylamido)ethyl}propanedioate (46)

Following the method of Example 7, Step A and replacing 1-amino-1-deoxy-β-D-glucopyranose with 1-amino-1-deoxy-β-D-mannopyranose (prepared according to the method described by Vetter et al., *Bioconjug. Chem.* 1995, 6, 316–318) afforded the title compound (46). $^1$H NMR (CD$_3$CN, 400 MHz): 7.3 (m, 10H), 5.1–5.19 (q, 4H), 3.7 (m, 1H), 3.64 (m, 2H), 3.5 (m, 2H), 3.42 (m, 1H), 3.2 (m, 1H), 3.0 (m, 1H), 2.3 (m, 2H), 2.14 (m, 2H). MS (ESI) m/z: 518.36 (M+H)$^+$.

Step B: {2-(β-D-Mannopyranos-1-ylamido) ethyl}propanedioic Acid (47)

Following the method of Example 7, Step B and replacing compound (40) with compound (46) afforded the title compound (47). MS (ESI) m/z: 338.32 (M+H)$^+$.

Step C: [1,R2R-Cyclohexanediamine-N,N'][{2-(β-D-Mannopyranos-1-ylamido)ethyl}propanedioato (2-)-O,O']Platinum(II) (45)

Following the method of Example 1 using compound (47) provided compound (45) as a white solid. MS (ESI) m/z: 645.37, 643.33 prominent isotopes.

Example 10

[1R,2R-Cyclohexanediamine-N,N'][{3-(β-D-Glucopyranos-1-ylamido)propyl}propanedioato(2-)-O,O']Platinum(II) (48)

Step A: Dibenzyl{3-(β-D-Glucopyranos-1-ylamido)propyl}propanedioate (49)

Following the method of Example 7, Step A and replacing compound (5) with compound (38) afforded the title compound (49). $^1$H NMR (CD$_3$CN, 400 MHz): 7.3 (m, 10H), 5.08–5.18 (q, 4H, J=12.4 Hz), 4.85 (d, 1H, J=9.2 Hz), 3.75 (m, 1H), 3.56 (m, 2H), 3.369 (m, 2H), 3.26 (m, 2H), 2.28 (m, 2H), 1.9 (m, 2H), 1.6 (m, 2H). MS (ESI) m/z: 532.38 (M+H)$^+$.

Step B: {3-(β-D-Glucopyranos-1-ylamido)propyl}propanedioic Acid (50)

Following the method of Example 7, Step B and replacing compound (40) with compound (49) afforded the title compound (50). $^1$H NMR (D$_2$O, 400 MHz): δ 4.84 (d, 1H, J=8.8 Hz), 3.71 (m, 1H), 3.56–3.6 (dd, 1H, J=5.6 Hz), 3.39 (m, 2H), 3.27 (m, 3H), 2.27 (m, 2H), 1.83 (m, 2H), 1.59 (m, 2H). MS (ESI) m/z: 352.3 (M+H)$^+$.

Step C: [1R,2R-Cyclohexanediamine-N,N'][{3-(β-D-Glucopyranos-1-ylamido)propyl}propanedioato(2-)-O,O']Platinum(II) (48)

Following the method of Example 1 using compound (50) provided the title compound (48) (0.13 g, 35%) as a white solid. $^1$H NMR (D$_2$O, 400 MHz): δ 5.71 (br, 2H), 5.07 (br, 2H), 4.94 (d, 1H, J=9.2 Hz), 3.85 (dd, 1H, J=2.4, 12.4 Hz), 3.70 (dd, 1H, J=5.2, 12.4 Hz), 3.63 (t, 1H, J=7.6 Hz), 3.45–3.54 (m, 2H), 3.3–3.46 (m, 2H), 2.30–2.50 (m, 6H), 2.02 (d, 2H, J=12.0 Hz), 1.62–1.80 (m, 2H), 1.48–1.63 (m, 2H), 1.20–1.36 (m, 2H), 1.04–1.20 (m, 2H). MS (ESI) m/z: 658.41, 659.42, 660.37 main isotopes.

Example 11

[1R,2R-Cyclohexanediamine-N,N'][{3-(β-D-Galactopyranos-1-ylamido)propyl}propanedioato(2-)-O,O']Platinum(II) (51)

Step A: Dibenzyl{3-(β-D-Galactopyranos-1-ylamido)propyl}propanedioate (52)

Following the method of Example 8, Step A and replacing compound (5) with compound (38) afforded the title compound (52). $^1$H NMR (CD$_3$CN, 400 MHz): 7.3 (m, 10H), 5.0–5.17 (q, 4H, J=12 Hz), 4.8 (m, 1H), 3.9 (m, 1H), 3.6 (m, 2H), 3.5 (m, 4H), 2.2 (m, 2H), 1.9 (m, 2H), 1.58 (m, 2H). MS (ESI) m/z: 532.4 (M+H)$^+$.

Step B: {3-(β-D-Galactopyranos-1-ylamido)propyl}propanedioic Acid (53)

Following the method of Example 7, Step B and replacing compound (40) with compound (52) afforded the title compound (53). $^1$H NMR (D$_2$O, 400 MHz): δ 4.76 (d, 1H, J=8.8 Hz), 3.8 (d, 1H, J=2.4 Hz), 3.62 (m, 1H), 3.57 (m, 2H), 3.5 (m, 1H), 3.49 (m, 1H), 3.24 (t, 1H), 2.26 (m, 2H), 1.72 (m, 2H), 1.5 (m, 2H). MS (ESI) m/z: 352.3 (M+H)$^+$.

Step C: [1R,2R-Cyclohexanediamine-N,N'][{3-(β-D-Galactopyranos-1-ylamido)propyl}propanedioato(2-)-O,O']Platinum(II) (51)

Following the method of Example 1 using compound (53) provided the title compound (51) (0.14 g, 74%) as a white solid. $^1$H NMR (D$_2$O, 400 MHz): δ 5.72 (br, 2H), 5.06 (br, 2H), 4.89 (d, 1H, J=8.8 Hz), 3.80–4.00 (m, 1H), 3.55–3.80 (m, 8H), 2.30–2.50 (m, 6H), 1.90–2.10 (m, 2H), 1.64–1.80 (m, 2H), 1.44–1.62 (m, 2H), 1.20–1.40 (m, 2H), 1.00–1.20 (m, 2H). MS (ESI) m/z: 658.34, 659.35, 660.37 main isotopes.

Example 12

[1R,2R-Cyclohexanediamine-N,N'][{3-(α,β-D-Galactopyranos-6-ylamido)propyl}propanedioato(2-)-O,O']Platinum(II) (54)

Step A: 6-Phthalimido-1,2:3,4-Di-O-Isopropylidene-α-D-Galactopyranose (55)

1,2:3,4-Di-O-isopropylidene-α-D-galactopyranose (0.27 mmol), phthalimide (0.3 mmol), and triphenylphosphine (0.3 mmol) were stirred together in THF under a nitrogen atmosphere, then diethylazodicarboxylate (0.3 mmol) was added dropwise and the mixture stirred at room temperature overnight. The solvent was removed in vacuo, the residue dissolved in CH$_2$Cl$_2$ and washed with NaHCO$_3$, and the organic phase purified by column chromatography on silica gel, eluting with 30% v/v ethyl acetate in hexane to afford the title compound (55) in 97% yield. $^1$H NMR (CD$_3$OD, 400 MHz): δ 7.8 (m, 4H), 5.4 (d, 1H), 4.65 (dd, 1H) 4.3 (m, 2H), 4.2 (m, 2H), 3.6 (dd, 1H), 1.5 (s, 3H), 1.4 (s, 3H), 1.35 (s, 3H), 1.25 (s, 3H). MS (ESI) m/z: 390.2 (M+H)$^+$.

Step B: 6-Amino-1,2:3,4-Di-O-Isopropylidene-α-D-Galactopyranose (56)

Compound (55) was treated with hydrazine (0.56 mmol, 1.1 eq) in ethanol (2 mL) at room temp for 2 h. The reaction mixture was washed with water, extracted with CH$_2$Cl$_2$, and concentrated in vacuo to obtain the title compound (56) in 93% yield. $^1$H NMR (CD$_3$OD, 400 MHz): δ 5.5 (d, 1H), 4.7 (dd, 1H), 4.42 (m, 1H), 4.3 (dd, 1H), 4.0 (m, 1H), 3.1 (m, 2H), 1.52 (s, 3H), 1.40 (s, 3H), 1.34 (s, 6H). MS (ESI) m/z: 260.3 (M+H)$^+$.

Step C: Dibenzyl{3-(1,2:3,4-Di-O-Isopropylidene-α-D-Galactopyranos-6-ylamido)propyl}propanedioate (57)

Compound (38) was dissolved in DMF (20 mL) and a slight excess of compound (56) and saturated aqueous NaHCO$_3$ to adjust the pH above 7.0 was added. The reaction mixture was stirred for 2 h then filtered to remove undissolved solids, and the resulting filtrate was then purified by column chromatography on silica gel using 40% ethyl acetate in hexane as eluent to afford the title compound (57) as a colorless oil in 75% yield. $^1$HNMR (CD$_3$OD, 400 MHz): 67.22 (m, 10H), 5.2 (d, 1H), 5.1 (q, 4H), 4.6 (dd, 1H), 4.3 (m, 1H), 4.2 (dd, 1H), 3.9 (m, 1H), 3.6 (t, 1H), 3.5 (m, 1H), 3.16 (m, 1H), 2.2 (t, 2H), 1.94 (t, 2H), 1.5 (m, 2H), 1.4 (d, 6H), 1.2 (d, 6H). MS (ESI) m/z: 612.4 (M+H)$^+$.

Step D: Dibenzyl 3-(α,β-D-Galactopyranos-6-ylamido)propyl}propanedioate (58)

Compound (57) was treated with a 7:3 v/v solution of TFA in water at room temperature for 4 h. After removal of most of solvent, the crude product was purified by preparative HPLC to give the title compound (58) as a mixture of α and β anomers in 43% yield. $^1$H NMR (CD$_3$OD, 400 MHz): δ 7.25 (m, 10H), 5.15 (m, 5H), 4.4 (dd), 4.0 (t), 3.75 (m, 2H), 3.59–3.4 (m, 4H), 2.2 (t, 2H), 1.98 (m, 2H), 1.6 (m, 2H). MS (ESI) m/z: 531.1 (M+H)$^+$.

Step E: 3-(α,β-D-Galactopyranos-6-ylamido) propyl}propanedioic Acid (59)

Compound (58) (4.3 mmol) was subjected to hydrogenolysis (hydrogen-filled balloon) in 1:1 ethyl acetate: ethanol in the presence of 10% of Pd/C for 4 h. The mixture was filtered through celite, washed with ethanol and water, and the combined filtrate concentrated in vacuo to a gummy syrup that was further dissolved in water and lyophilized to provide the title compound (59) as a white powder. $^1$H NMR (CD$_3$OD, 400 MHz): δ 5.1 (dd, α anomer), 4.35 (dd, β anomer), 3.9 (m), 3.72 (d), 3.7–3.55 (dd, 2H), 3.53–3.49 (m, 3H), 3.3 (m, 2H), 3.3–3.2 (m, 1H), 2.1 (t, 2H), 1.7 (m, 2H), 1.5 (m, 2H). MS (ESI) m/z: 352.2 (M+H)$^+$.

Step F: [1R,2R-Cyclohexanediamine-N,N'][{3-(α,β-D-Galactopyranos-6-ylamido)propyl}propanedioato(2-)-O,O']Platinum(II) (54)

Following the method of Example 1 and using compound (59) provided compound (54) (0.55 g, 73%) as a white solid having a ratio of α and β anomers of ~2:3. $^1$H NMR (D$_2$O, 400 MHz): 5.19 (d, J=3.6 Hz, α anomer), 4.52 (d, J=8.0 Hz, β anomer), 4.01–4.12 (m), 3.91 (d, J=3.2 Hz, α anomer), 3.85 (d, J=3.6 Hz, β anomer), 3.59–3.82 (m, 3H), 3.32–3.57 (m, 2.5H), 2.30–2.50 (m, 6H), 2.01 (d, 2H, J=12.4 Hz), 1.68 (q, 2H, J=7.6 Hz), 1.50–1.62 (m, 2H), 1.20–1.38 (m, 2H), 1.03–1.20 (m, 2H). MS (ESI) m/z: 658.34, 659.35, 660.37 main isotopes.

Example 13

[Diammine][{3-(α,β-D-Galactopyranos-6-ylamido)propyl}propanedioato(2-)-O,O']Platinum(II) (60)

Following the method of Example 2 and using compound (59) provided the title compound (60) (0.35 g, 52%) as a white solid having a ratio of α and β anomers of ~1.6:1. $^1$H NMR (D$_2$O, 400 MHz): 5.1 (d, α-anomer), 4.4 (d, β anomer), 3.9 (m, α anomer), 3.77 (d, β anomer), 3.75 (dd), 3.6–3.4 (m, 3H), 3.3–3.1 (m, 3H), 2.2 (m, 4H), 1.6 (m, 2H). MS (ESI) m/z: 578.16, 579.17, 580.19 main isotopes.

Example 14

[1R,2R-Cyclohexanediamine-N,N'][{3-(α,β-D-Mannopyranos-6-ylamido)propyl}propanedioato(2-)-O,O']Platinum(II) (61)

Step A: 6-Amino-6-Deoxy-Methyl-α-D-Mannopyranoside (62)

A mixture of methyl-α-D-mannopyranoside (20 mmol), sodium azide (22 mmol) and triphenylphosphine (19.5 mmol) in CCl$_4$-DMF (1:4 v/v, 100 mL) was stirred at 75° C. for 16 h. CCl$_4$ was removed in vacuo, triphenylphosphine (22 mmol) in H$_2$O-DMF (1:25 v/v, 100 mL) was added to the reaction mixture, and the mixture was stirred at room temperature for 2 days. After removal of solvent, the residue was partitioned between dichloromethane and 0.1 M aqueous HCl solution. The product in aqueous phase was concentrated in vacuo and purified by reverse phase preparative HPLC to afford the title compound (62) (1.5 g).

Step B: Dibenzyl 3-(Methyl-α-D-Mannopyranos-6-ylamido)propyl}-propanedioate (63)

To a solution of compound (62) (1 mmol) and sodium bicarbonate (3 mmol) in H$_2$O (2 mL) was added a solution of compound (38) (1 mmol) in DMF (4 mL) and the mixture stirred at room temperature for 2 h. After removal of solvent, the residue was partitioned between ethyl acetate and 10% citric acid. The organic phase was dried over MgSO$_4$, concentrated to dryness and the resulting residue was purified by reverse phase preparative HPLC to afford the title compound (63) (410 mg).

Step C: Dibenzyl 3-(β-D-Mannopyranos-6-ylamido) propyl}propanedioate (64)

To a solution of compound (63) (0.5 mmol) in ethyl acetate (5 mL) was added a 1.0 M solution of boron tribromide (10 mL) in dichloromethane at 0° C. The reaction mixture was further stirred at room temperature for 30 min. The reaction mixture was then neutralized by addition of sodium carbonate, the solvent removed in vacuo, and the product partitioned between ethyl acetate and 10% citric acid. The organic phase was dried over MgSO$_4$, concentrated in vacuo and the resulting residue was purified by reverse phase preparative HPLC to afford the title compound (64) (109 mg).

Step D: 3-(β-D-Mannopyranos-6-ylamido) propyl}propanedioic Acid (65)

Compound (64) (0.2 mmol) was dissolved in ethanol and treated with 5% Pd—C and hydrogen at room temperature for 6 h. After filtration through celite, the filtrate was concentrated in vacuo and the resulting residue purified by reverse phase preparative HPLC to afford the title compound (65) (41 mg). $^1$H NMR (D$_2$O, 400 MHz): 4.95 (d, 1H, J=1.6 Hz), 3.63–3.88 (m, 2H), 3.22–3.50 (m, 5H), 2.18 (t, 2H), 1.68–1.76 (m, 2H), 1.44–1.58 (m, 2H).

Step E: [1R,2R-Cyclohexanediamine-N,N'][{3-(α,β-D-Mannopyranos-6-ylamido)propyl}propanedioato(2-)-O,O']Platinum(II) (61)

Following the method of Example 1 and using compound (65) provided compound (61) (70 mg, 81%) as a white solid having a ratio of α and β anomers of ~1:6. $^1$H NMR (D$_2$O, 400 MHz): 5.12 (d, 1H, J=1.6 Hz), 3.74–3.98 (m, 2H), 3.38–3.68 (m, 5H), 2.30–2.52 (m, 6H), 2.02 (d, 2H, J=12.4 Hz), 1.70 (q, 2H, J=7.2 Hz), 1.50–1.60 (m, 2H), 1.20–1.38 (m, 2H), 1.04–1.20 (m, 2H). MS (ESI) m/z: 658.41, 659.42, 660.37 main isotopes.

Example 15

[1R,2R-Cyclohexanediamine-N,N'][{3-(α,β-D-Glucopyranos-6-ylamido)propyl}propanedioato(2-)-O,O']Platinum(II) (66)

Following the method of Example 14 and substituting methyl-α-D-glucopyranoside for methyl-α-D-mannopyranoside in Step A provided the title compound (66) having a ratio of α and β anomers of 2:3. $^1$H NMR (D$_2$O, 400 MHz): 5.60 (br, 2H), 5.00 (d, J=4.0 Hz, α anomer), 4.96 (br, 2H), 4.47 (d, J=8.0 Hz, β anomer), 3.70–3.78 (m), 2.43–3.60 (m, 2.4H), 3.24–3.42 (m, 2.6H), 3.04–3.20 (m, 1.6H), 2.20–2.40 (m, 6H), 1.89 (d, 2H, J=12.8 Hz), 1.58 (q, 2H, J=7.2 Hz), 1.44 (d, 2H, J=8.8 Hz), 1.10–1.24 (m, 2H), 0.95–1.10 (m, 2H). MS (ESI) m/z: 658.41, 659.35, 660.37 main isotopes.

Example 16

[1R,2R-Cyclohexanediamine-N,N'][{3-(Methyl-α-D-Glucopyranos-6-ylamido)propyl}propanedioato(2-)-O,O']Platinum(II) (67)

Following the method of Example 15 but eliminating the BBr$_3$-mediated demethylation step provided the title compound (67). $^1$H NMR (D$_2$O, 400 MHz): 3.26–3.55 (m, 5H), 3.24 (s, 3H), 3.11–3.16 (m, 1H), 2.22–2.32 (m, 6H), 1.89 (d, 2H, J=12.8 Hz), 1.58 (q, 2H, J=7.2 Hz), 1.44 (d, 2H, J=8.8 Hz), 1.10–1.20 (m, 2H), 0.98–1.05 (m, 2H). MS (ESI) m/z. 670.45, 671.43, 674.45 main isotopes.

Example 17

[1R,2R-Cyclohexanediamine-N,N'][{2-(Methyl-α-D-Glucopyranos-6-yl-carbonyl)ethyl}propanedioato(2-)-O,O']Platinum(II) (68)

Step A: Dibenzyl{2-(Methyl-α-D-Glucopyranos-6-yl-carbonyl)ethyl}-propanedioate (69)

Compound (4) (0.43 mmol), methyl-2, 3, 4-tri-O-benzyl-α-D-glucopyranoside (0.43 mmol), DCC (0.86 mmol), and DMAP (0.22 mmol) were dissolved in DMF (5 mL) and stirred at room temperature overnight. After concentration in vacuo, the residue was dissolved in ethyl acetate and washed successively with saturated aqueous NH$_4$Cl, brine and water and the product purified by flash chromatography on silica gel (eluting with 2:1 v/v hexane/EtOAc) to afford the title compound (69) (250 mg) as a colorless oil. $^1$H NMR (CDCl$_3$, 400 MHz): 7.20–7.40 (m, 25H), 4.45–5.20 (m, 11H), 3.26–4.30 (m, 6H), 3.34 (s, 3H), 2.30–2.50 (m, 2H), 2.18–2.30 (m, 2H).

Step B: {2-(Methyl-α-D-Glucopyranos-6-yl-carbonyl)ethyl}propanedioic Acid (70)

A solution of compound (69) (250 mg) in EtOH (20 mL) and AcOH (5 mL) was stirred under a hydrogen atmosphere (balloon) in the presence of 10% Pd/C (25 mg) for 4 h. After removal of the catalyst by filtration through celite, the filtrate was purified by preparative HPLC to provide the title compound (70) (29 mg) as a white solid. $^1$H NMR (CD$_3$OD, 400 MHz): 4.65 (d, 1H), 4.40 (dd, 1H), 4.21 (dd, 1H), 3.65–3.76 (m, 1H), 3.58 (t, 1H), 3.36–3.50 (m, 1H), 3.39 (s, 3H), 3.25–3.35 (m, 1H), 2.46 (t, 2H), 2.14 (q, 2H).

Step C: [1R,2R-Cyclohexanediamine-N,N'][{2-(Methyl-α-D-Glucopyranos-6-yl-carbonyl)ethyl}propanedioato(2-)-O,O']Platinum(II) (68)

Following the method of Example 1 and using compound (70) provided compound (68) (17 mg, 54%) as a white solid. $^1$H NMR (D$_2$O, 400 MHz): 5.95 (br, 1H), 5.74 (br, 1H), 5.26 (br, 1H), 4.98 (br, 1H), 4.62 (d, 1H, J=4.0 Hz), 4.31 (dd, 1H, J=2.4, 12.0 Hz), 4.18 (dd, 1H, J=4.8, 12.0 Hz), 3.95 (t, 1H, J=6.8 Hz), 3.57–3.65 (m, 1H), 3.54 (t, J=9.2 Hz), 3.34–3.44 (m, 2H), 3.32 (s, 3H), 2.43 (t, 2H, J=7.2 Hz), 2.10–2.40 (m, 4H), 1.88(br, 2H), 1.46 (br, 2H), 1.00–1.25 (m, 4H). MS (ESI) m/z: 658.41, 659.35, 660.37 main isotopes.

Example 18

[1R,2R-Cyclohexanediamine-N,N'][{2-(Methyl-α-D-Mannopyranos-6-yl-carbonyl)ethyl}propanedioato(2-)-O,O']Platinum(II) (71)

Step A: Dibenzyl{2-(Methyl-α-D-Mannopyranos-6-yl-carbonyl)ethyl}-propanedioate (72)

Compound (4) (0.39 mmol) was treated with SOCl$_2$ (1 mL) at 80° C. for 1 h. After complete removal of the excess SOCl$_2$ in vacuo, the crude product was dissolved in THF (2 mL) and cooled 0° C. in an ice bath. Methyl-2,3,4-tri-O-benzyl-α-D-mannopyranoside (0.39 mmol) and DMAP (0.39 mmol) were added and the mixture stirred at 40° C. overnight. EtOAc (10 mL) was added and washed successively with saturated aqueous NH$_4$Cl, brine, and water and the product purified by flash chromatography on silica gel (eluting with 2:1 v/v hexane/EtOAc) to afford the title compound (72) (100 mg) as a colorless oil. $^1$H NMR (CDCl$_3$, 400 MHz): 5.00–5.20 (m, 6H), 4.90 (d, 1H), 4.70 (s, 2H), 4.59 (s, 2H), 4.53 (d, 1H), 4.35 (dd, 1H), 4.26 (dd, 1H), 3.80–3.90 (m, 1H), 3.70–3.80 (m, 1H), 3.57 (t, 1H), 3.24 (s, 3H), 2.30–2.50 (m, 2H), 2.20–2.30 (m, 2H).

Step B: {2-(Methyl-α-D-Mannopyranos-6-yl-carbonyl)ethyl}propanedioic Acid (73)

Following the method of Example 17, Step B, and replacing compound (69) with compound (72) afforded the title compound (73) as a white solid. $^1$H NMR (CD$_3$OD, 400 MHz): 4.60 (d, 1H), 4.42 (dd, 1H), 4.22 (dd, 1H), 3.78 (m, 1H), 3.54–3.70 (m, 3H), 3.41 (t, 1H), 3.36 (s, 3H), 2.47 (t, 2H), 2.15 (q, 2H).

Step C: [1R,2R-Cyclohexanediamine-N,N'][{2-(Methyl-α-D-Mannopyranos-6-yl-carbonyl)ethyl}propanedioato(2-)-O,O"Platinum(II) (71)

Following the method of Example 1 and using compound (73) provided compound (71) (10 mg, 49%) as a white solid. $^1$H NMR (D$_2$O, 400 MHz): 5.12 (d, 1H, J=1.6 Hz), 3.74–3.98 (m, 2H), 3.38–3.68 (m, 5H), 2.30–2.52 (m, 6H), 2.02 (d, 2H, J=12.4 Hz), 1.70 (q, 2H, J=7.2 Hz), 1.50–1.60 (m, 2H), 1.20–1.38 (m, 2H), 1.04–1.20 (m, 2H). MS (ESI) m/z: 658.41, 659.42, 660.37 main isotopes.

Example 19

[1R,2R-Cyclohexanediamine-N,N'][{2-(α,β-D-Glucuron-6-yl-amido)ethyl}propanedioato(2-)-O,O']Platinum(II) (74)

Step A: 1,2,3,4-Tetra-O-Acetyl-D-Glucuronic acid (75)

D-Glucuronic acid (3 mmol) in acetic anhydride (5 mL) was stirred in the presence of a catalytic amount of Sc(OTf)$_3$ (0.15 mmol) at room temperature for 2 h. The resulting solution was cooled in an ice bath and carefully quenched by addition of water (2 mL). After stirring at r.t. for 30 min, the reaction mixture was frozen at −78° C. and lyophilized to afford the crude title compound (75) as a yellow colored solid, which was used in next step without further purification.

Step B: Dibenzyl 2-Aminoethylpropanedioate (17)

2-(N-Boc-amino)ethyl bromide (10 mmol) and dibenzyl malonate (10 mmol) were stirred in DMF (50 mL) containing potassium carbonate (22 mmol) at r.t. overnight. EtOAc (200 mL) and 1N HCl (100 mL) were added and the organic layer was separated and washed successively with saturated aqueous $NH_4Cl$, brine, and water. After removal of the solvent, the crude product was dissolved in $CH_2Cl_2$ (20 mL) and treated with TFA (5 mL) at r.t. for 1 h. Removal of the solvent in vacuo provided the title compound (17) as its TFA salt (5.0 g). $^1H$ NMR ($CD_3OD$, 400 MHz): δ 7.2–7.4 (m, 10H), 5.16 (s, 4H), 3.5 (t, 1H), 3.0 (t, 2H), 2.28 (q, 2H).

Step C: {2-(α,β-D-Glucuron-6-yl-amido)ethyl}propanedioic Acid (76)

Compound (75) (4 mmol) and N-hydroxysuccinimide (4 mmol) were dissolved in a mixture of THF (20 mL) and acetonitrile (20 mL), DCC (4 mmol) was added, and the reaction mixture was stirred overnight. After removal of the precipitate by filtration and evaporation of the solvent, the crude NHS ester was dissolved in DMF (10 mL) and an excess of compound (17) added, using saturated aqueous $NaHCO_3$ to adjust the pH above 7.0. The reaction mixture was stirred for 2 h then filtered to remove solids, the resulting filtrate diluted with ethyl acetate (20 mL), and stirred under a hydrogen atmosphere in the presence of 10 wt % Pd/C for 4 h. Mass spectrometry analysis indicated formation of tri- and tetra-acetyl products, which were hydrolyzed by treatment with 1N LiOH in aqueous methanol at r.t. to form the title compound (76) as a white solid (500 mg, 1.5:1 mixture of α and β anomers). $^1H$ NMR (D20, 400 MHz): δ 5.21 (d, 1H, α anomer), 4.62 (d, 1H, β anomer), 4.13 (d, 1H, α anomer), 3.80 (d, 1H, β anomer), 3.40–3.75 (m, 4H), 3.20–3.36 (m, 2H), 2.07 (q, 2H).

Step D: [1R,2R-Cyclohexanediamine-N,N'][{2-(α,β-D-Glucuron-6-yl-amido)ethyl}propanedioato(2-)-O,O']Platinum(II) (74)

Following the method of Example 1 and using compound (76) provided compound (74) (75% yield), a white solid, as a 1:1 mixture of anomers. $^1H$ NMR ($D_2O$, 400 MHz): δ 5.24 (d, J=4.0 Hz, α anomer), 4.66 (d, J=8.4 Hz, β anomer) 4.19 (d, J=9.6 Hz), 3.96–4.00 (m, 1H), 3.90 (d, J=9.6 Hz), 3.72 (t, J=9.6 Hz), 3.45–3.62 (m, 2H), 3.26–3.40 (m, 2.5H), 2.2–2.45 (m, 4H), 1.99 (d, 2H, J=12.4 Hz), 1.53 (d, 2H, J=9.2 Hz), 1.20–1.32 (m, 2H), 1.00–1.20 (m, 2H). MS (ESI) m/z: 630.44, 631.39, 632.40 main isotopes.

Example 20

[1R,2R-Cyclohexanediamine-N,N'][{2-(α,β-D-Galacturon-6-yl-amido)ethyl}propanedioato(2-)-O,O']Platinum(II) (77)

Following the method of Example 19 and replacing D-glucuronic acid with D-galacturonic acid provided the title compound (77) (75% yield), a white solid, as a 1:1 mixture of anomers. $^1H$ NMR ($D_2O$, 400 MHz): δ 5.34 (d, J=3.6 Hz, α anomer), 4.63 (d, J=7.6 Hz, β anomer) 4.52 (d, J=1.2 Hz), 4.20–4.30 (m), 4.20–4.22 (m, 1H), 3.90–3.93 (m, 1H), 3.91 (dd, J=3.2, 10.0 Hz), 3.81 (dd, J=4.0, 10.0 Hz), 3.70 (dd, J=3.6, 10.0 Hz), 3.50 (dd, J=8.0, 10.0 Hz), 3.3–3.5 (m, 2H), 2.30–2.40 (m, 2H), 2.10–2.30 (m, 2H), 2.01(d, 2H, J=12.8 Hz), 1.54 (d, 2H, J=8.4 Hz), 1.20–1.30 (m, 2H), 1.00–1.20 (m, 2H). MS (ESI) m/z: 630.37, 631.39, 632.40, main isotopes.

Example 21

[1R,2R-Cyclohexanediamine-N,N'][{2-(Methyl-β-D-Glucuron-6-yl-amido)ethyl}propanedioato(2-)-O,O']Platinum(II) (78)

Following the method of Example 19, replacing compound (75) with methyl β-D-glucuronic acid in Step C and omitting the LiOH hydrolysis step afforded the title compound (78) (113 mg) as a white solid. $^1H$ NMR ($D_2O$, 400 MHz): δ 5.62–5.82 (br. s, 2H), 4.90–5.20 (br. s, 2H), 4.42 (d, 1H, J=8.0 Hz), 4.01 (t, 1H, J=7.6 Hz), 3.87 (d, 1H, J=9.6 Hz), 3.60 (t, 1H, J=9.6 Hz), 3.55 (s, 3H), 3.52 (t, 1H, J=8.8 Hz), 3.26–3.40 (m, 3H), 2.26–2.42 (br, 2H), 2.23–2.26 (m, 2H), 2.00 (br, 2H), 1.55 (br, 2H), 1.20–1.35 (m, 2H), 1.52 (br, 2H). MS (ESI) m/z: 644.18, 645.13, 646.21 main isotopes.

Example 22

[1R,2R-Cyclohexanediamine-N,N'][{3-(α,β-D-Glucopyranos-2-yl-amido)propyl}propanedioato(2-)-O,O']Platinum(II) (79)

Step A: Dibenzyl{3-(α,β-D-Glucopyranos-2-yl-amido)propyl}propanedioate (80)

Compound (38) (2.7 mmol) was dissolved in DMF (16 mL) and D-glucosamine hydrochloride (4 mmol) was added followed by saturated aqueous $NaHCO_3$ to adjust the pH above 7.0. The reaction mixture was stirred for 2 h at r.t. and solids were removed by filtration. The pH of the filtrate was adjusted to ~5.0 by addition of 1 N HCl, the solvent removed in vacuo, and the residue purified by preparative HPLC to afford the title compound (80) (1.24 g, 86%) as a colorless oil. $^1H$ NMR ($CD_3OD$, 400 MHz): δ 7.24 (m, 10H), 5.08 (d, 1H), 5.11 (q, 4H), 3.75–3.90 (m, 3H), 3.64–3.74 (m, 2H), 3.55 (t, 1H), 3.25–3.40 (m, 1H), 2.26 (t, 2H), 1.90–2.00 (m, 2H), 1.60–1.70 (m, 2H).

Step B: {3-(α,β-D-Glucopyranos-2-yl-amido)propyl}propanedioic Acid (81)

Compound (80) (1.69 mmol) was stirred under an atmosphere of hydrogen with Pd/C (90 mg) in a mixture of EtOAc (20 mL), MeOH (20 mL) and water (5 mL) for 3 h. The catalyst was removed by filtration and the crude product was purified by preparative HPLC to afford the title compound (81) (580 mg, 98%) as a mixture of anomers. $^1H$ NMR ($CD_3OD$, 400 MHz): δ 5.18 (d, 1H), 4.60 (d, 1H), 3.54–3.90 (m, 3H), 3.20–3.50 (m, 3H), 2.20–2.40 (m, 2H), 1.80–2.00 (m, 2H), 1.60–1.80 (m, 2H).

Step C: [1R,2R-Cyclohexanediamine-N,N'][{3-(α,β-D-Glucopyranos-2-yl-amido)propyl}propanedioato(2-)-O,O']Platinum(II) (79)

Following the method of Example 1 and using compound (81) provided compound (79) (153 mg, 75% yield), a white solid, as a 3:2 mixture of α and β anomers. $^1H$ NMR ($D_2O$, 400 MHz): δ 5.22 (d, J=3.6 Hz, α anomer), 4.68 (d, J=8.4 Hz, β anomer), 3.65–3.92 (m, 4H), 3.35–3.65 (m, 3H), 2.30–2.60 (m, 6H), 2.00 (d, 2H, J=12.8 Hz), 1.68 (q, 2H, J=7.6 Hz), 1.54 (d, 2H, J=8.0 Hz), 1.20–1.35 (m, 2H), 1.02–1.20 (m, 2H). MS (ESI) m/z: 658.27, 659.22, 660.17 main isotopes.

Example 23

[Diammine][{3-(α,β-D-Glucopyranos-2-yl-amido)propyl}propanedioato(2-)-O,O']Platinum(II) (82)

Following the method of Example 2 and using compound (81) provided compound (82) (350 mg, 71% yield), a white solid, as a 1.6:1 mixture of α and β anomers. $^1$H NMR (D$_2$O, 400 MHz): δ 5.19 (d, α anomer), 4.68 (d, β anomer), 4.19 (br, 6H), 3.60–3.92 (m, 5H), 3.40–3.55 (m, 2H), 2.32–2.50 (m, 4H), 1.68 (q, 2H).

Example 24

[1R,2R-Cyclohexanediamine-N,N'][{3-(α,β-D-Mannopyranos-1-yl)propyl}propanedioato(2-)-O,O']Platinum(II) (83)

Step A: 1-Trifluoroacetoxy-2,3,4,6-Tetra-O-Benzyl-α,β-D-Mannopyranoside (84)

2,3,4,6-tetra-O-benzyl-α-D-mannopyranose (1.5 g) was treated with trifluoroacetic anhydride (30 mL) until the mixture became a homogeneous solution. The solvent was removed in vacuo and the resulting crude product (84) (1.7 g) was used directly in the next step without further purification. $^1$H NMR (CDCl$_3$, 400 MHz): δ 7.30–7.23 (m, 16H), 7.15–7.09 (m, 4H), 6.21 (d, 1H, J=2.0 Hz), 4.83 (d, 1H), 4.73–4.48 (m, 7H), 4.07 (dd, 1H, J=9.6 Hz), 3.85–3.63 (m, 5H).

Step B: 3-Bromopropyl-2,3,4,6-Tetra-O-Benzyl-α,β-D-Mannopyranoside (85)

To a solution of compound (84) (1.7 g, 2.7 mmol) and 3-bromo-1-propanol (0.26 mL, 2.9 mmol) in dichloromethane (20 mL) was added a few drops of boron trifluoride diethyl etherate. The resulting solution was stirred at room temperature for 2 h and the solvent removed in vacuo. The residue was purified by flash chromatography on silica gel, eluting with 10% ethyl acetate in hexane to afford the title compound (85) (1.40 g, 79%). $^1$H NMR (CDCl$_3$, 400 MHz): δ 7.36–7.13 (m, 20H), 4.87–4.47 (m, 8H), 3.97–3.37 (m, 9H), 2.05–2.00 (m, 2H).

Step C: Dibenzyl{3-(2,3,4,6-Tetra-O-Benzyl-α,β-D-Mannopyranos-1-yl)propyl}propanedioate (86)

To a stirred solution containing compound (85) (1.4 g, 2.1 mmol) and dibenzyl malonate (1.0 mL, 4.2 mmol) in dry DMF (20 mL) was added potassium carbonate (0.7 g, 5.0 mmol). The resulting mixture was stirred at room temperature until the starting material was completely consumed (monitored by TLC). After completion of the reaction, the mixture was poured into water (30 mL) and extracted with a 1:1 mixture of diethyl ether and ethyl acetate (2×30 mL). The combined organic solvents were then successively washed with water (2×30 mL) and brine. The organic layer was concentrated in vacuo and the residue purified by flash chromatography on silica gel, eluting with a gradient of 10%–25% ethyl acetate in hexane to afford the title compound (86) as a viscous colorless liquid (1.50 g, 82%). $^1$H NMR (CDCl$_3$, 400 MHz): δ 7.35–7.12 (m, 30H), 5.13 (s, 4H), 4.86–4.47 (m, 8H), 3.98–3.30 (m, 9H), 1.98–1.92 (m, 2H), 1.56–1.52 (m, 2H).

Step D: 3-(α,β-D-Mannopyranos-1-yl)propyl}propanedioic Acid (87)

A high-pressure reactor was charged with compound (86) (1.5 g, 1.7 mmol) in a 1:1 mixture of methanol and ethyl acetate (5 mL), 10 wt. % palladium on activated carbon (0.30 g), and 1N HCl (1.0 mL). The reactor was then placed under hydrogen atmosphere (55 psi) for two hours while shaking. The catalyst was filtered off and the solvents were removed in vacuo. The residue was further purified by preparative HPLC to give the title compound (87) (0.30 g, 54%). $^1$H NMR (CD$_3$OD, 400 MHz): δ 4.76 (m, 0.85H), 4.52 (d, 0.15H, J=2.8 Hz), 3.88–3.70 (m, 5H), 3.63 (m, 1H), 3.55 (m, 1H), 3.48 (m, 1H), 3.40–3.32 (m, 1H), 1.96 (m, 2H), 1.69 (m, 2H). MS (ESI) m/z 323.12 (M–H)$^-$.

Step E: [1R,2R-Cyclohexanediamine-N,N'][{3-(α,β-D-Mannopyranos-1-yl)propyl}propanedioato(2-)-O,O']Platinum(II) (83)

Following the method of Example 1 and using compound (87) provided compound (83) (395 mg, 70% yield), as a white solid. $^1$H NMR (D$_2$O, 400 MHz): δ 4.77 (d, 1H, J=1.6 Hz), 3.90–3.94 (m, 1H), 3.50–3.86 (m, 8H), 2.18–2.40 (m, 4H), 1.90 (d, 2H, J=12.0 Hz), 1.61 (q, 2H, J=6.8 Hz), 1.10–1.24 (m, 2H), 0.94–1.10 (m, 2H). MS (ESI) m/z 631.39, 632.40, 634.43 main isotopes.

Example 25

[1R,2R-Cyclohexanediamine-N,N'][{2-(α,β-D-Glucopyranos-1-yl)ethyl}propanedioato(2-)-O,O']Platinum(II) (88)

Step A: 1-Trifluoroacetoxy-2,3,4,6-Tetra-O-Benzyl-α,β-D-Glucopyranoside (89)

Following the method of Example 24, Step A, and replacing 2,3,4,6-tetra-O-benzyl-α-D-mannopyranose with 2,3,4,6-tetra-O-benzyl-D-glucopyranose provided the title compound (89) in quantitative yield. $^1$H NMR (CDCl$_3$, 400 MHz): δ 7.30–7.08 (m, 20H), 6.35 (d, 1H, J=3.2 Hz), 4.92–4.46 (m, 8H), 3.93–3.86 (m, 2H), 3.75–3.62 (m, 4H).

Step B: 2-Bromoethyl-2,3,4,6-Tetra-O-Benzyl-α,β-D-Glucopyranoside (90)

Following the method of Example 24, Step B, and replacing compound (84) with compound (89) and 3-bromo-1-propanol with 2-bromoethanol afforded the title compound (90) (0.80 g, 33%). $^1$H NMR (CDCl$_3$, 400 MHz): δ 7.32–7.09 (m, 20H), 5.02–4.48 (m, 9H), 4.01–3.45 (m, 10H).

Step C: Dibenzyl{2-(2,3,4,6-Tetra-O-Benzyl-α,β-D-Glucopyranos-1-yl)ethyl}propanedioate (91)

Following the method of Example 24, Step C, and replacing compound (85) with compound (90) provided the title compound (91) (0.67 g, 64%). $^1$H NMR (CDCl$_3$, 400 MHz): δ 7.34–7.09 (m, 30H), 5.15–4.39 (m, 13H), 3.92–3.38 (m, 9H), 2.26 (m, 2H).

Step D: 2-(α,β-D-Glucopyranos-1-yl)ethyl]propanedioic Acid (92)

Following the method of Example 24, Step D, and replacing compound (86) with compound (91) provided the title compound (92). $^1$H NMR (CD$_3$OD, 400 MHz): δ 4.81 (d, 0.85H, J=3.6 Hz), 4.29 (d, 0.15H, J=8.0 Hz), 3.91–3.81 (m, 2H), 3.75–3.53 (m, 4H), 3.44–3.31 (m, 4H), 2.24 (m, 2H). MS (ESI) m/z 309.11 (M–H)$^-$.

Step E: [1R,2R-Cyclohexanediamine-N,N'][{2-(α,β-D-Glucopyranos-1-yl)ethyl}propanedioato(2-)-O,O'] Platinum(II) (88)

Following the method of Example 24, Step E, and replacing compound (87) with compound (92) provided the title compound (88) (119 mg, 75%), a white solid, as a 4:1 mixture of α and β anomers. $^1$H NMR (D$_2$O, 400 MHz): δ 4.79 (d, J=3.6 Hz, α anomer), 4.34 (d, J=8.0 Hz, β anomer), 4.18 (t, 0.8H, J=7.2 Hz), 4.02 (t, 0.2H, J=7.6 Hz), 3.12–3.90 (m, 7H), 2.30–2.45 (m, 2H), 2.20–2.30 (m, 2H), 1.82–1.96 (m, 2H), 1.44 (d, 2H, J=9.6 Hz), 1.15–1.24 (m, 2H), 0.95–1.15 (m, 2H). MS (ESI) m/z 617.37, 618.38, 619.33 main isotopes.

Example 26

[1R,2R-Cyclohexanediamine-N,N'][{2-(α,β-D-Galactopyranos-1-yl)ethyl}propanedioato(2-)-O,O'] Platinum(II) (93)

Step A: 1-Trifluoroacetoxy-2,3,4,6-Tetra-O-Benzyl-α,β-D-Galactopyranoside (94)

Following the method of Example 24, Step A, and replacing 2,3,4,6-tetra-O-benzyl-α-D-mannopyranose with 2,3,4,6-tetra-O-benzyl-D-galactopyranose provided the title compound (94) in quantitative yield as a 92:8 mixture of α and β anomers. $^1$H NMR (CDCl$_3$, 400 MHz): δ 7.33–7.19 (m, 20H), 6.38 (d, J=3.2 Hz, α anomer), 5.62 (d, J=7.6 Hz, β anomer), 4.90 (d, 1H, J=12 Hz), 4.81–4.67 (m, 4H), 4.54–4.39 (m, 3H), 4.20 (dd, 1H, J=3.6, 10 Hz), 4.03 (t, 1H, J=6.0 Hz), 3.98 (m, 1H), 3.86 (dd, 1H, J=2.8 Hz, J=10 Hz), 3.54 (dd, 1H, J=6, 9.6 Hz), 3.46 (dd, 1H, J=6.8, 9.6 Hz).

Step B: 2-Bromoethyl-2,3,4,6-Tetra-O-Benzyl-α,β-D-Galactopyranoside (95)

Following the method of Example 24, Step B, and replacing compound (84) with compound (94) and 3-bromo-1-propanol with 2-bromoethanol afforded the title compound (95), which was used in the next step without further purification.

Step C: Dibenzyl{2-(2,3,4,6-Tetra-O-Benzyl-α,β-D-Galactopyranos-1-yl)ethyl}propanedioate (96)

Following the method of Example 24, Step C, and replacing compound (85) with compound (95) provided the title compound (96) (53% yield). $^1$H NMR (CDCl$_3$, 400 MHz): δ 7.34–7.19 (m, 30H), 5.14–4.34 (m, 13H), 4.0–3.85 (m, 4H), 3.74–3.68 (m, 2H), 3.69–3.37 (m, 3H), 2.26 (m, 2H).

Step D: 2-(α,β-D-Galactopyranos-1-yl)ethyl}propanedioic Acid (97)

Following the method of Example 24, Step D, and replacing compound (86) with compound (96) provided the title compound (97) as a 3:1 mixture of α and β anomers. $^1$H NMR (CD$_3$OD, 400 MHz): δ 4.88 (d, J=2.8 Hz, α anomer), 4.28 (d, J=7.2 Hz, β anomer), 3.97–3.56 (m, 9H), 3.40 (m, 1H), 2.28 (m, 2H). MS (ESI) m/z 309.11 (M–H)$^-$.

Step E: [1R,2R-Cyclohexanediamine-N,N'][{2-(α,β-D-Glucopyranos-1-yl)ethyl}propanedioato(2-)-O,O'] Platinum(II) (93)

Following the method of Example 24, Step E, and replacing compound (87) with compound (97) provided the title compound (93) (136 mg), a white solid, as a 4:1 mixture of α and β anomers. $^1$H NMR (D$_2$O, 400 MHz): δ 4.83 (d, J=3.6 Hz, α anomer), 4.28 (d, J=7.2 Hz, β anomer), 3.84–3.92 (m, 2H), 3.45–3.80 (m, 6H), 2.55–2.68 (m, 1H), 2.38–2.50 (m, 1H), 1.90 (d, 2H, J=12.0 Hz), 1.45 (d, 2H, J=8.0 Hz), 1.15 (br, 2H), 0.94–1.10 (m, 2H). MS (ESI) m/z 617.37, 618.38, 619.40 main isotopes.

Example 27

Determination of In Vitro Cytotoxicity of Test Compounds

The effect of experimental compounds on cancer cell growth and viability was measured in a panel of human cancer cells grown in vitro. All cancer cell lines were obtained from the American Tissue Type Collection (ATTC). Cells were maintained in the following media: TUR, H69AR, Calu-6, ME180, and PC3 cells were grown in RPMI medium containing 4.5 g/L glucose, 10% FBS, 4 mM L-glutamine, and 1 mM sodium pyruvate); and HT29 cells were grown in DMEM with 4.5 g/L glucose, 10% FBS, and 6 mM L-glutamine. All cells were grown at 37° C. in 5% CO$_2$ and passaged bi-weekly.

For cytoxicity studies, cells were seeded into 96-well clear-bottom microtiter plates at the following densities: TUR (7,500 cells/well), HT29 (5,000 cells/well), H69AR (10,000 cells/well), Calu-6 (15,000 cells/well), and ME180 (2,500 cells/well). Cells were maintained at 37° C. with 5% CO$_2$ for 24 hours prior to addition of various experimental compounds. Each condition was measured in triplicate. For compounds dissolved in DMSO, the final DMSO concentration in each well and in the non-drug treated control cells was constant and below 1% in all studies. The number of viable cells was determined after 24, 48, and 72 hours using Alamar blue fluorescence. Briefly, Alamar blue (10 mM) was added to each well for 4 hours, and the number of viable cells estimated by measuring the fluorescence of reduced Alamar blue (530 nm excitation, 590 nm emission). To correct for background fluorescence, cells were treated with 100% DMSO to eliminate all viable cells. The effect of drug on cell growth was determined by calculating the fraction of live cells treated with drug compared to untreated cells: $(Fl_{drug\ treated} - Fl_{DMSO\ killed})/(Fl_{untreated} - Fl_{DMSO\ killed})$. The half maximal growth inhibition value (GI50) was calculated using commercial curve-fitting software (Prism) and data for selected compounds is shown in Table 2.

TABLE 2

In Vitro Growth Inhibition for Platinum Sugar Complexes

| | GI50 (μM) | | | | | |
|---|---|---|---|---|---|---|
| Compound | Calu-6 48 h | H69AR 48 h | HT29 48 h | ME180 48 h | PC3 48 h | TUR 48 h |
| Cisplatin | 149 | 4 | 30 | 1 | 31 | 10 |
| Carboplatin | 712 | 94 | 515 | 64 | 290 | 123 |
| Oxaliplatin | 52 | 60 | 133 | 28 | 113 | 42 |
| (42) | 131 | 188 | 860 | 4 | 45 | 22 |

TABLE 2-continued

In Vitro Growth Inhibition for Platinum Sugar Complexes

| | GI50 (μM) | | | | | |
|---|---|---|---|---|---|---|
| Compound | Calu-6 48 h | H69AR 48 h | HT29 48 h | ME180 48 h | PC3 48 h | TUR 48 h |
| (45) | —* | 84 | — | — | — | 28 |
| (51) | 255 | 286 | 374 | 5 | 84 | 37 |
| (54) | 185 | 77 | 238 | 15 | 85 | 9 |
| (60) | — | 79 | — | — | — | 117 |
| (66) | 163 | 102 | 222 | 7 | — | 15 |
| (67) | 68 | 185 | 234 | 5 | — | 21 |
| (74) | — | 53 | — | — | — | 53 |
| (77) | — | 38 | — | — | — | 38 |
| (78) | — | 76 | 103 | — | — | 15 |
| (79) | — | 55 | 124 | — | 67 | 15 |
| (82) | 300 | 112 | 800 | 11 | 133 | 142 |
| (83) | 155 | 163 | 117 | 10 | 100 | 41 |
| (88) | 260 | 98 | 226 | 13 | 112 | 31 |
| (93) | 139 | 78 | 178 | 7 | 69 | 20 |

*not measured.

Example 28

Effect of Sugar Transport Inhibitors on In Vitro Cytotoxicity

To demonstrate the participation of cellular uptake mechanisms for the platinum-containing compounds, an inhibitor of sugar transport (phloridzen) was also included in the media of cells exposed to the experimental agents. The data presented in Table 3 demonstrate that increasing concentrations of phloridzen block the cytotoxic effects of compound (54) while having no influence on the activity of the non-transported compound cisplatin at 48 hours.

TABLE 3

GI50 (μM) of Uptake in HT29 Cells

| | mM Phloridzen | | | |
|---|---|---|---|---|
| Compound | 0 | 0.2 | 0.5 | 1.0 |
| (54) | 385 | 574 | 759 | >1000 |
| Cisplatin | 261 | 194 | 192 | 254 |

Example 29

In Vivo Tumor Growth Inhibition by Platinum Sugar Complexes

Tumor xenograft studies were performed using nude athymic CD-1 mice (Charles River Laboratories). Human cancer cells ($5 \times 10^6$ PC3, $5 \times 10^6$ HT29, $10^7$ Calu-6, and $5 \times 10^6$ ME180) were implanted in the hind flank of nude mice. Tumor growth was measured using calipers and tumor volume calculated using the formula: (width$^2$×(length/2)). Tumor volume was measured 3 days per week. Animal weight was measured 3 days per week to assess compound toxicity.

Compounds were tested for in vivo tumor growth inhibition as follows. Animals bearing tumors 100–200 mg were sorted into groups (5–8 animals) with similar average tumor mass per group. Drug doses were administered by intraperitoneal (IP) injection (0.5 mL). Test compounds were dissolved in phosphate buffered saline (PBS) and concentration adjusted for animal weight. Actual drug concentrations in formulated doses were verified by quantitative nitrogen detection. Animals were dosed every 7 days for 21 days in most studies. In several studies, animals were dosed twice weekly (days 0, 4, 7, 10, 14, etc.). Tumor volume and animal weight were measured on days 0, 2, 4, 7, 9, 11, 14, 16, 18, 21, 23, 25, and 28. At the end of the study, animal blood was removed for analysis of liver and kidney function (BUN, creatine, AST and ALT; analytical measurements performed by Quality Clinical Labs). Tumor volume at the end of the study was calculated as a percentage of the tumor volume on day 0. The percent tumor growth inhibition was obtained from the ratio of the percentage tumor volume increase in drug treated animals to the percentage tumor volume increase in saline treated animals. Data for selected compounds is shown in Table 4. This data indicates that compound (54) is effective in inhibiting growth of several different tumor types in vivo, with activity equivalent or superior to that of the clinically useful anticancer platinum agents cisplatin, oxaliplatin, and carboplatin.

TABLE 4

Percent Tumor Growth Inhibition in Mouse Xenograft Model

| Compound | Dose (mg/kg) | PC3 (Prostate) | HT29 (Colon) | Calu-6 (Lung) | ME180 (Cervical) |
|---|---|---|---|---|---|
| Cisplatin | 2 | — | 69 | — | — |
| Oxaliplatin | 5 | — | 40 | — | — |
| Carboplatin | 100 | — | 47 | 56 | 25 |
| (79) | 80 (2/week) | 48 | — | — | — |
| (54) | 80 (2/week) | 82 | — | — | — |
| (54) | 50 (2/week) | — | — | 73 | 24 |
| (54) | 75 (2/week) | — | 74 | — | 24 |
| (54) | 100 | — | 63 | 42 | 18 |
| (54) | 500 | — | — | 81 | 68 |

Example 30

Determination of Maximum Tolerated Doses (MTD) and Therapeutic Indices

To determine the maximum tolerated doses for compound (54) relative to clinically used platinum anticancer agents, nude mice were injected with increasing drug doses (0.5 mL, intraperitoneally) on days 0, 7, and 14. The maximal tolerated dose was defined as the highest drug dose that resulted in less than 10% animal weight loss. The therapeutic index of a given drug is defined as the ratio of the maximum tolerated dose to the minimally effective dose. Table 5 indicates that compound (54) has a dramatically improved therapeutic index relative to the clinically useful anticancer compounds cisplatin, carboplatin, and oxaliplatin.

TABLE 5

Maximum Tolerated Doses (MTD) and Therapeutic Indices

| | MTD | | Minimal Effective Dose | | Therapeutic Index |
|---|---|---|---|---|---|
| Compound | mg/kg | μmol/kg | mg/kg | μmol/kg | MTD/Min Eff |
| Cisplatin | 6 | 30 | 2 | 7 | 2.9 |
| Carboplatin | 90 | 226 | 40 | 100 | 2.3 |
| Oxaliplatin | 10 | 27 | 5 | 13 | 2.0 |
| (54) | 500 | 760 | 40 | 60 | 12.7 |

Example 31

Tumor Growth Inhibition by Sugar Platinum Complexes

Female CD® Nu/Nu mice (approx. 20 g) were obtained from Charles River (Hollister, Calif.). The mice were housed five mice/cage in shoebox cages with stainless steel, suspended, wire-mesh lids. All animals were acclimated for a minimum of one week on site prior to study initiation. Labdiet® irradiated (Certified Rodent Diet # 5001, PMI Nutrition International, Inc.) and sterilized water was provided ad libitum. Fluorescent lighting was provided for approximately 12 hours per day via an automatic timer. Temperature and humidity were monitored and recorded daily. Individual mice were ear punched for identification. Mice from each group were identified by cage card with study number, animal number, group number, and sex.

HT29 colonic tumor cells were thawed and cultured in DMEM medium in T-flasks. When the flasks were 85% confluent, the cells were harvested in HBSS buffer at a final concentration of $2.5 \times 10^7$ cells/mL. DLD1 cells (colonic tumor cells) and Calu-6 cells (lung tumor cells) were grown in RPMI 1640 medium and cells were harvested at $1.25 \times 10^7$ cells/mL. Each mouse received 0.2 mL of this cell suspension subcutaneously.

Tumor cells were diluted to the desired dose concentration and mixed to maintain an even suspension. Using a one mL syringe, mice were inoculated subcutaneously on the dorsal side of the right hind limb with 0.2 mL of media-containing cells.

Tumors were measured three times a week using vernier calipers. When the tumor volume reached approximately 200 mm³ the mice were randomized and distributed into different treatment groups.

The first date of dosing was defined as day 0. The maximal tolerated dose was determined for each compound, and efficacy studies were performed using doses that caused 5–15% weight loss, with no mortality, after two weeks with a dose at day 0 and day 7, e.g., an equitoxic dose (see, for example, Arp, *Toxicol Pathol.* 1999, 27 (1), 121–122). All compounds were dissolved in physiological saline solution based on the corresponding dosage and administered intraperitoneally at 10 mL/kg animal body weight once a week for four weeks. The dosing schedule used for the HT29, DLD1, and Calu-6 tumor models is shown in Tables 6–8, respectively. For each compound, the dose of compound in mg/kg dissolved in 10 mL/kg is indicated. The amount of compound and the dose volume was based on the weight of each animal at the time of dosing.

TABLE 6
Dosing Schedule for the HT-29 Tumor Model.

| Compound | No. of Mice | Dose Volume (mL/kg) | Dose of Compound (mg/kg) |
| --- | --- | --- | --- |
| (60) | 7 | 10 | 675 |
| (88) | 7 | 10 | 130 |
| (78) | 7 | 10 | 190 |
| Oxaliplatin | 7 | 10 | 7 |

TABLE 7
Dosing Schedule for the DLD1 Tumor Model

| Compound | No. of Mice | Dose Volume (mL/kg) | Dose of Compound (mg/kg) |
| --- | --- | --- | --- |
| (54) | 5 | 10 | 280 |
| (88) | 5 | 10 | 160 |
| (78) | 5 | 10 | 200 |
| Saline | 5 | 10 | 0 |
| Oxaliplatin | 5 | 10 | 7.5 |

TABLE 8
Dosing Schedule for the Calu-6 Tumor Model

| Compound | No. of Mice | Dose Volume (mL/kg) | Dose of Compound (mg/kg) |
| --- | --- | --- | --- |
| Saline | 7 | 10 | 0 |
| (54) | 7 | 10 | 390 |
| (60) | 7 | 10 | 540 |
| (88) | 7 | 10 | 130 |
| Oxaliplatin | 7 | 10 | 7 |
| (78) | 7 | 10 | 190 |
| (42) | 7 | 10 | 360 |

All animals were observed at least twice a day for morbidity, mortality, injury, and availability of food and water. Tumor volume and animal body weight were measured and recorded thee time per week. The tumor volume was calculated using the formula:

$$\text{tumor volume} = (\text{width} \times (\text{length}/2))$$

At the end of the study, all mice were euthanized by carbon dioxide inhalation and removed from the study.

Tumor volume and body weight were measured every three days until the experiments were terminated. Test compounds were compared to oxaliplatin tumor efficacy. Data is reported as the average percent increase in tumor volume or as tumor volume (mm³) from the first day of dosing. Compounds were evaluated in three tumor models: HT29 (colon), DLD1 (colon), and Calu-6 (lung). The results are shown in FIGS. 1–4. In each tumor model, several platinum-containing compounds were observed to cause greater long-term tumor growth suppression than oxaliplatin when dosed at an equitoxic level.

Figure 2:
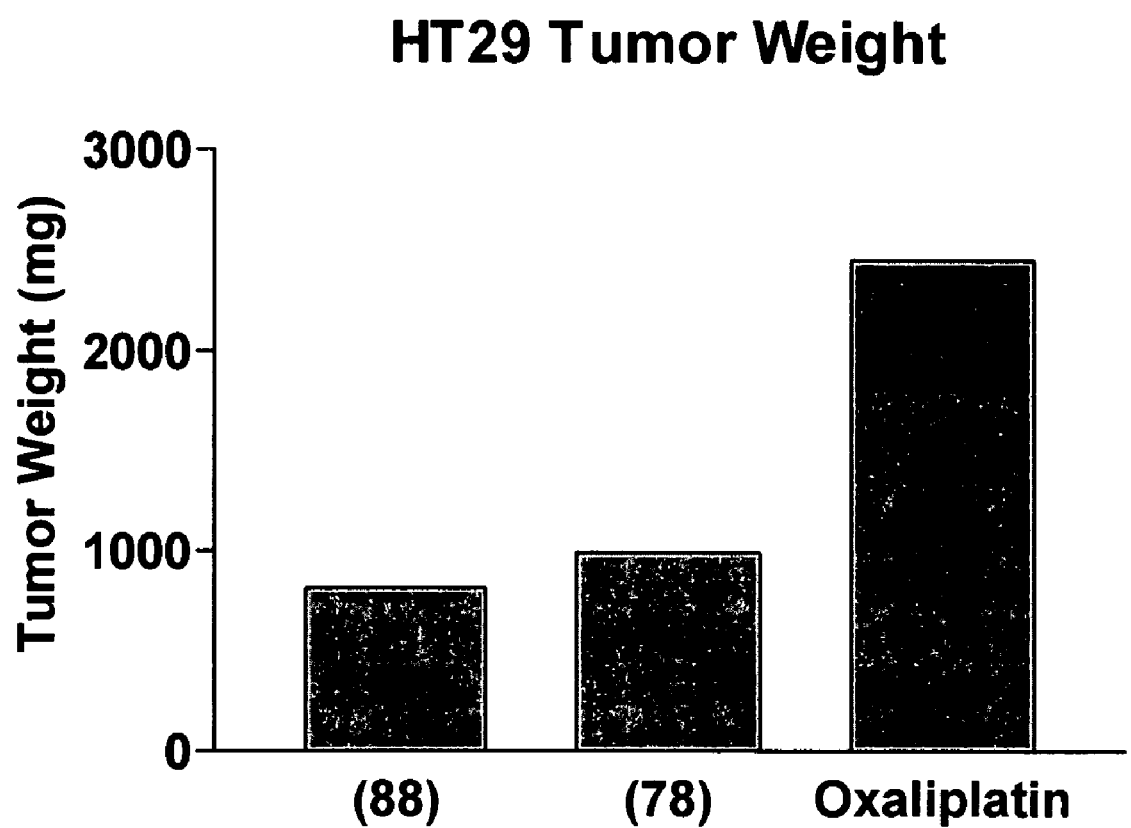
FIG. 2 shows the average tumor weight in a HT29 colon tumor xenograph model after treatment with oxaliplatin or certain sugar platinum compounds of the present disclosure.
Figure 3:
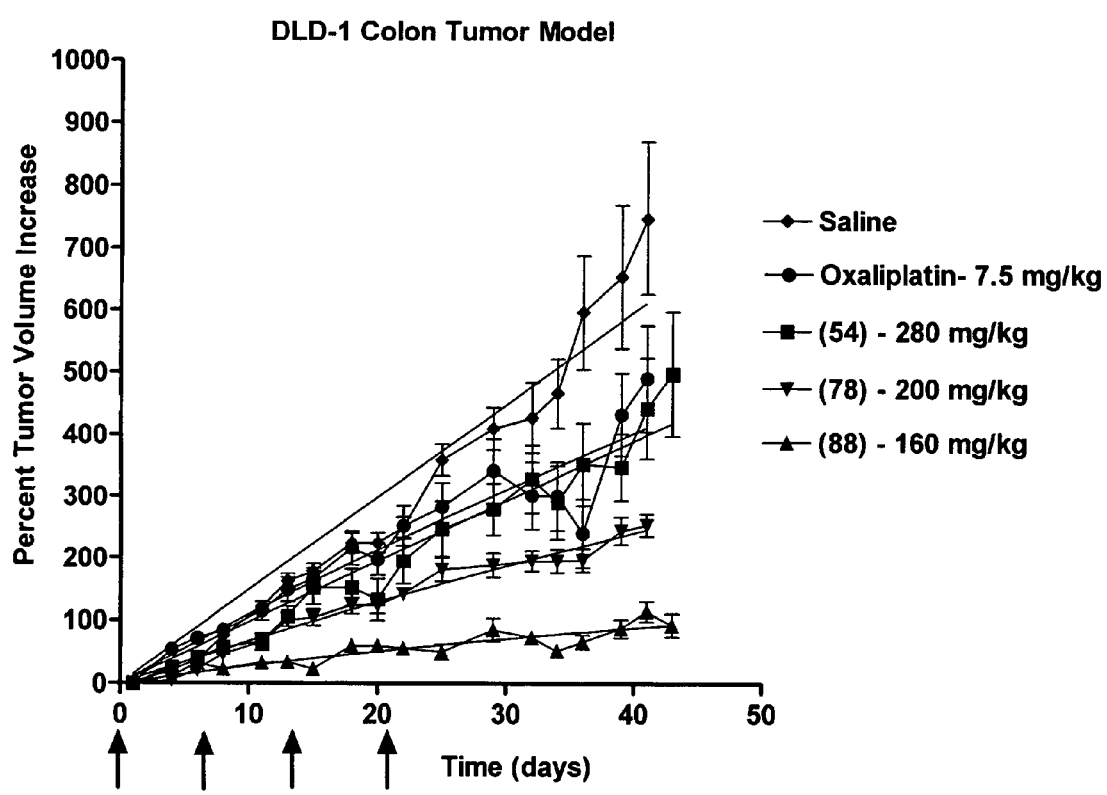
FIG. 3 shows percent tumor size in a DLD-1 colon tumor xenograph model during treatment with oxaliplatin or certain sugar platinum compounds of the present disclosure.
Figure 4:
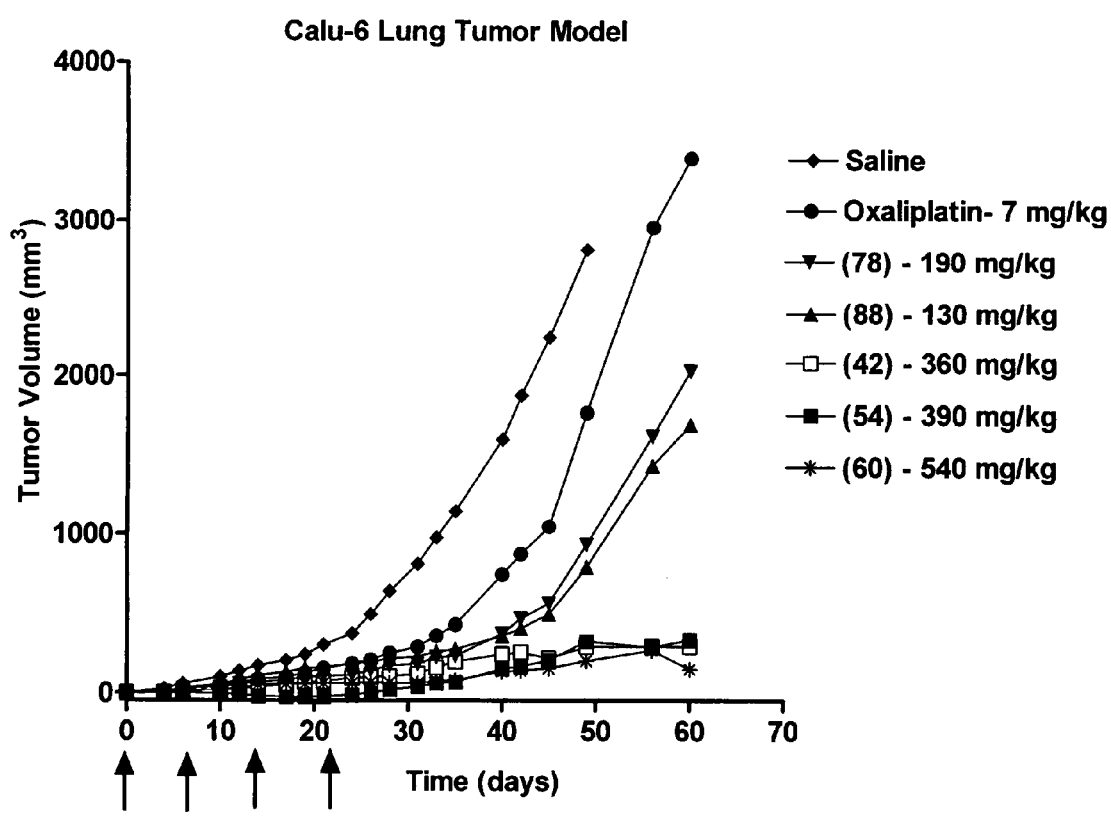
FIG. 4 shows percent tumor size in a Calu-6 lung tumor xenograph model during treatment with oxaliplatin or certain sugar platinum compounds of the present disclosure.

Antitumor efficacy of platinum-containing compounds on human colon cancer HT29 xenograft tumors in nude mice is shown in FIGS. 1 and 2. FIG. 1 shows the tumor growth during treatment with saline, oxaliplatin, (60), (78), or (88). Arrows indicate days on which dosing was performed. FIG. 2 shows the average measured tumor weight after termination of the HT29 study. Antitumor efficacy of platinum-containing compounds on human colon cancer DLD1 xenograft tumors in nude mice is shown in FIG. 3. Antitumor efficacy of platinum-containing compounds on lung cancer Calu-6 xenograft tumors in nude mice is shown in FIG. 4.

While certain embodiments have been shown and described, various modifications and substitutions may be made thereto without departing from the spirit and scope of the invention. Accordingly, it is to be understood that the present invention has been described by way of illustration and not limitation.

What is claimed is:

1. A compound of Formula (I):

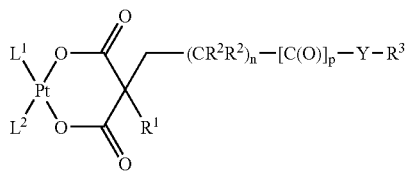

(I)

or a pharmaceutically acceptable salt thereof, or a pharmaceutically acceptable solvate of any of the foregoing, wherein:

n is an integer from 0 to 4;
p is chosen from 0 and 1;
$L^1$ and $L^2$ are each $NH_3$ or $L^1$ and $L^2$ together form a 1,2-cycloalkanediamine chosen from trans-(1R,2R)-cyclohexanediamine, trans-(1S,2S)-cyclohexanediamine, and cis-(R,S)-cyclohexanediamine;
$R^1$ is chosen from hydrogen and $C_{1-4}$ alkyl;
each $R^2$ is independently chosen from hydrogen and $C_{1-4}$ alkyl;
Y is chosen from —$NR^5$— and —O—;
$R^3$ is chosen from

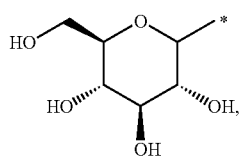

(II)

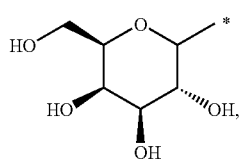

(III)

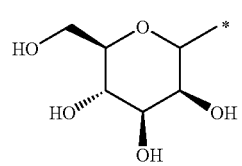

(IV)

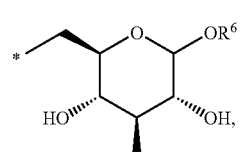

(V)

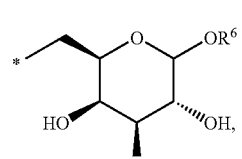

(VI)

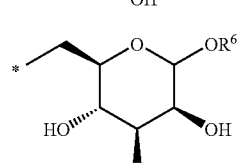

(VII)

-continued

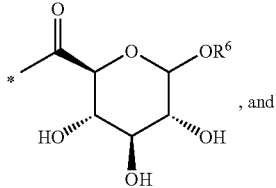

(VIII)

, and

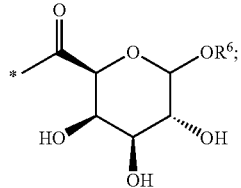

(IX)

wherein $R^6$ is chosen from hydrogen and $C_{1-4}$ alkyl; and $R^5$ is chosen from hydrogen and $C_{1-4}$ alkyl.

2. The compound of claim 1, wherein $R^1$ is hydrogen.

3. The compound of claim 1, wherein each $R^2$ is hydrogen.

4. The compound of claim 1, wherein n is chosen from 1 and 2.

5. The compound of claim 1, wherein Y is chosen from —NH— and —O—.

6. The compound of claim 1, wherein $R^6$ is chosen from hydrogen and methyl.

7. The compound of claim 1, wherein $L^1$ and $L^2$ are each $NH_3$ or $L^1$ and $L^2$ together are trans-(1R,2R)-cyclohexanediamine.

8. The compound of claim 1, wherein $L^1$ and $L^2$ together are trans-(1R,2R)-cyclohexanediamine.

9. The compound of claim 1, wherein $R^1$ is hydrogen and each $R^2$ is hydrogen.

10. The compound of claim 1, wherein $R^1$ is hydrogen, each $R^2$ is hydrogen, and n is chosen from 1 and 2.

11. The compound of claim 1, wherein $R^1$ is hydrogen, each $R^2$ is hydrogen, and Y is —NH—.

12. The compound of claim 1, wherein $R^1$ is hydrogen, each $R^2$ is hydrogen, n is chosen from 1 and 2, and Y is —NH—.

13. The compound of claim 1, wherein $R^1$ is hydrogen, each $R^2$ is hydrogen, n is chosen from 1 and 2, and Y is —O—.

14. A compound of Formula (X):

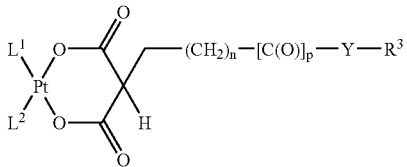

(X)

or a pharmaceutically acceptable salt thereof, or a pharmaceutically acceptable solvate of any of the foregoing, wherein:

n is chosen from 1 and 2;
p is chosen from 0 and 1;
$L^1$ and $L^2$ are each $NH_3$ or $L^1$ and $L^2$ together are trans-(1R,2R)-cyclohexanediamine;
Y is chosen from —NH— and —O—; and
$R^3$ is chosen from

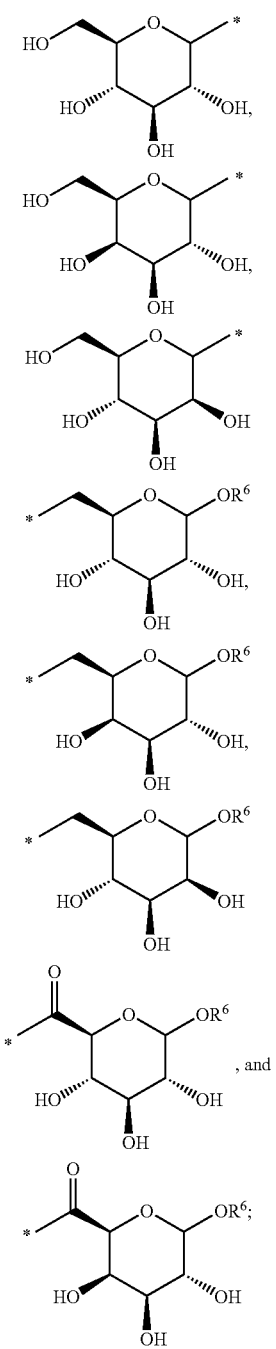

wherein R⁶ is chosen from hydrogen and methyl.

15. The compound of claim 14, wherein Y is —NH—.

16. The compound of claim 14, wherein Y is —O—.

17. A compound chosen from:

[1R,2R-Cyclohexanediamine-N,N'][{2-(β-D-Glucopyranos-1-ylamido)ethyl}propanedioato(2-)-O,O']Platinum(II);

[1R,2R-Cyclohexanediamine-N,N'][{2-(β-D-Galactopyranos-1-ylamido)ethyl}propanedioato(2-)-O,O']Platinum (II);

[1R,2R-Cyclohexanediamine-N,N'][{2-(β-D-Mannopyranos-1-ylamido)ethyl}propanedioato(2-)-O,O']Platinum (II);

[1R,2R-Cyclohexanediamine-N,N'][{3-(β-D-Glucopyranos-1-ylamido)propyl}propanedioato(2-)-O,O']Platinum (II);

[1R,2R-Cyclohexanediamine-N,N'][{3-(β-D-Galactopyranos-1-ylamido)propyl}propanedioato(2-)-O,O']Platinum (II);

[1R,2R-Cyclohexanediamine-N,N'] [{3-(α,β-D-Galactopyranos-6-ylamido)propyl}propanedioato(2-)-O,O']Platinum(II);

[Diammine][{3-(α,β-D-Galactopyranos-6-ylamido) propyl}propanedioato(2-)-O,O']Platinum(II);

[1R,2R-Cyclohexanediamine-N,N'][{3-(α,β-D-Mannopyranos-6-ylamido)propyl}propanedioato(2-)-O,O']Platinum(II);

[1R,2R-Cyclohexanediamine-N,N'][{3-(α,β-D-Glucopyranos-6-ylamido)propyl}propanedioato(2-)-O,O']Platinum (II);

[1R,2R-Cyclohexanediamine-N,N'][{3-(Methyl-α-D-Glucopyranos-6-ylamido)propyl}propanedioato(2-)-O,O'] Platinum(II);

[1R,2R-Cyclohexanediamine-N,N'][{2-(Methyl-α-D-Glucopyranos-6-yl-carbonyl)ethyl}propanedioato(2-)-O,O'] Platinum(II);

[1R,2R-Cyclohexanediamine-N,N'][{2-(Methyl-α-D-Mannopyranos-6-yl-carbonyl)ethyl}propanedioato(2-)-O, O']Platinum(II);

[1R,2R-Cyclohexanediamine-N,N'][{2-(α,β-D-Glucopyranos-1-yl)ethyl}propanedioato(2-)-O,O']Platinum(II);

[1R,2R-Cyclohexanediamine-N,N'][{2-(α,β-D-Galactopyranos-1-yl)ethyl}propanedioato(2-)-O,O']Platinum(II);

[1R,2R-Cyclohexanediamine-N,N'][{2-(α,β-D-Glucuron-6-yl-amido)ethyl}propanedioato(2-)-O,O']Platinum(II);

[1R,2R-Cyclohexanediamine-N,N'][{2-(α,β-D-Galacturon-6-yl-amido)ethyl}propanedioato(2-)-O,O']Platinum(II);

[1R,2R-Cyclohexanediamine-N,N'][{2-(Methyl-β-D-Glucuron-6-yl-amido)ethyl}propanedioato(2-)-O,O']Platinum(II); and

[1R,2R-Cyclohexanediamine-N,N'][{3-(α,β-D-Mannopyranos-1-yl)propyl}propanedioato(2-)-O,O']Platinum (II);

or a pharmaceutically acceptable salt thereof, or a pharmaceutically acceptable solvates of any of the foregoing.

18. A pharmaceutical composition comprising a therapeutically effective amount of a compound of claim 1 and a pharmaceutically acceptable vehicle.

19. The pharmaceutical composition of claim 18, wherein the compound is present in an amount effective for treating cancer in a patient.

20. A method of treating cancer in a patient comprising administering to a patient in need of such treatment a therapeutically effective amount of a compound of claim 1.

21. A method of treating cancer in a patient comprising administering to a patient in need of such treatment a therapeutically effective amount of a pharmaceutical composition of claim 18.

22. A compound of Formula (XI):

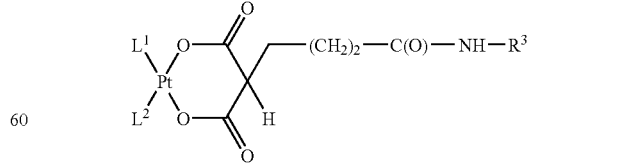

(XI)

or a pharmaceutically acceptable salt thereof, or a pharmaceutically acceptable solvate of any of the foregoing, wherein:

$L^1$ and $L^2$ are each $NH_3$ or $L^1$ and $L^2$ together form a 1,2-cycloalkanediamine chosen from trans-(1R,2R)- cyclohexanediamine, trans-(1S,2S)-cyclohexanediamine, and cis-(R,S)-cyclohexanediamine; and R 3 is

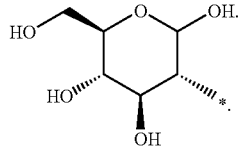

23. The compound of claim 22, wherein $L^1$ and $L^2$ are each $NH_3$ or $L^1$ and $L^2$ together are trans-(1R,2R) cyclohexanediamine.

24. A compound chosen from:

[1R,2R-Cyclohexanediamine-N,N'][{3-(α,β-D-Glucopyranos-2-yl-amido)propyl}propanedioato(2-)-O,O']Platinum (II); and

[Diammine][{3-(α,β-D-Glucopyranos-2-yl-amido)propyl}propanedioato(2-)-O,O']Platinum(II);

or a pharmaceutically acceptable salt thereof, or a pharmaceutically acceptable solvate of any of the foregoing.

* * * * *